US009714420B2

(12) United States Patent
Metzger et al.

(10) Patent No.: US 9,714,420 B2
(45) Date of Patent: Jul. 25, 2017

(54) RAPID CELL PURIFICATION SYSTEMS

(71) Applicant: Accelerate Diagnostics, Inc., Tucson, AZ (US)

(72) Inventors: Steven W. Metzger, Tucson, AZ (US); Kenneth Robert Hance, Tucscon, AZ (US)

(73) Assignee: Accelerate Diagnostics, Inc., Tucson, AZ (US)

( * ) Notice: Subject to any disclaimer, the term of this patent is extended or adjusted under 35 U.S.C. 154(b) by 90 days.

(21) Appl. No.: 15/003,604

(22) Filed: Jan. 21, 2016

(65) Prior Publication Data

US 2016/0138067 A1    May 19, 2016

Related U.S. Application Data

(62) Division of application No. 14/004,145, filed as application No. PCT/US2012/028139 on Mar. 7, 2012, now Pat. No. 9,434,937.

(Continued)

(51) Int. Cl.
*C12N 13/00* (2006.01)
*B03C 5/00* (2006.01)
(Continued)

(52) U.S. Cl.
CPC .............. *C12N 13/00* (2013.01); *B03C 5/005* (2013.01); *C12M 47/12* (2013.01); *C12Q 1/02* (2013.01);
(Continued)

(58) Field of Classification Search
None
See application file for complete search history.

(56) References Cited

U.S. PATENT DOCUMENTS 2,666,355 A    1/1954  Trurnit
3,493,772 A    2/1970  Daughters, II et al.
(Continued)

FOREIGN PATENT DOCUMENTS

AU    772760    5/2004
EP    498920    8/1992
(Continued)

OTHER PUBLICATIONS

Baker et al., "The Bactericidal Action of Synthetic Detergents," *J Exp Med.* 74:611-620, 1941.
(Continued)

*Primary Examiner* — Janet L Andres
*Assistant Examiner* — Stuart W Snyder
(74) *Attorney, Agent, or Firm* — KLARQUIST SPARKMAN, LLP

(57) ABSTRACT

Methods and systems for purifying cells and/or viruses are provided. The sample is added to a well disposed in a medium. A potential is applied across the medium to cause the contaminants to enter one or more walls of the well, and retain the cells and/or viruses in the well. The cells and/or viruses can be removed from the well, and optionally adhered or fixed to a surface, or detected. In one embodiment, the cells and/or viruses may be retained in the well by embedding in the medium. The medium including the embedded cells and/or viruses may be excised or otherwise removed and transferred to a glass slide or other solid surface.

12 Claims, 15 Drawing Sheets

Related U.S. Application Data

(60) Provisional application No. 61/449,824, filed on Mar. 7, 2011.

(51) Int. Cl.
*C12M 1/00* (2006.01)
*C12Q 1/02* (2006.01)
*G01N 1/34* (2006.01)
*G02B 21/36* (2006.01)
*C12Q 1/24* (2006.01)
*G01N 33/49* (2006.01)
*C12N 7/02* (2006.01)
*C12N 7/00* (2006.01)

(52) U.S. Cl.
CPC .............. *C12Q 1/24* (2013.01); *G01N 1/34* (2013.01); *G01N 33/491* (2013.01); *G02B 21/361* (2013.01); *B03C 2201/18* (2013.01); *B03C 2201/26* (2013.01); *C12N 7/00* (2013.01); *C12N 7/02* (2013.01); *C12N 2710/00051* (2013.01)

(56) References Cited

U.S. PATENT DOCUMENTS

| | | |
|---|---|---|
| 3,532,790 A | 10/1970 | Greenberg et al. |
| 3,637,313 A | 1/1972 | Upatnieks |
| 3,792,081 A | 2/1974 | Higuchi et al. |
| 3,811,036 A | 5/1974 | Perry |
| 3,832,532 A | 8/1974 | Praglin et al. |
| 3,854,480 A | 12/1974 | Zaffaroni |
| 3,904,293 A | 9/1975 | Gee |
| 3,926,564 A | 12/1975 | Giaever |
| 3,935,073 A | 1/1976 | Waters |
| 3,938,515 A | 2/1976 | Leeper et al. |
| 3,957,362 A | 5/1976 | Mancini et al. |
| 3,961,628 A | 6/1976 | Arnold |
| 4,069,307 A | 1/1978 | Higuchi et al. |
| 4,070,248 A | 1/1978 | Schmidt |
| 4,076,591 A | 2/1978 | Heden |
| 4,136,250 A | 1/1979 | Mueller et al. |
| 4,199,449 A | 4/1980 | Slejko |
| 4,199,499 A | 4/1980 | Smithwick, Jr. et al. |
| 4,200,493 A | 4/1980 | Wilkins et al. |
| 4,220,152 A | 9/1980 | Dresback |
| 4,224,439 A | 9/1980 | Ayers et al. |
| 4,233,847 A | 11/1980 | Walker |
| 4,246,343 A | 1/1981 | Wilkins et al. |
| 4,259,442 A | 3/1981 | Gayral |
| 4,282,287 A | 8/1981 | Giese |
| 4,288,543 A | 9/1981 | Sielaff et al. |
| 4,313,734 A | 2/1982 | Leuvering |
| 4,325,910 A | 4/1982 | Jordan |
| 4,330,440 A | 5/1982 | Ayers et al. |
| 4,332,476 A | 6/1982 | Stenberg et al. |
| 4,351,337 A | 9/1982 | Sidman |
| 4,357,142 A | 11/1982 | Schall, Jr. et al. |
| 4,363,634 A | 12/1982 | Schall, Jr. |
| 4,383,757 A | 5/1983 | Phillips |
| 4,390,343 A | 6/1983 | Walter |
| 4,423,099 A | 12/1983 | Mueller et al. |
| 4,450,150 A | 5/1984 | Sidman |
| RE31,712 E | 10/1984 | Giese |
| 4,478,822 A | 10/1984 | Haslam et al. |
| 4,478,914 A | 10/1984 | Giese |
| 4,481,137 A | 11/1984 | Ohnishi et al. |
| 4,487,839 A | 12/1984 | Kamentsky |
| 4,500,778 A | 2/1985 | Kusaka et al. |
| 4,508,832 A | 4/1985 | Carter et al. |
| 4,509,841 A | 4/1985 | Sakai et al. |
| 4,521,522 A | 6/1985 | Lundstrom et al. |
| 4,537,861 A | 8/1985 | Elings et al. |
| 4,540,881 A | 9/1985 | Hayashi et al. |
| 4,548,990 A | 10/1985 | Mueller et al. |
| 4,558,012 A | 12/1985 | Nygren et al. |
| 4,588,624 A | 5/1986 | Nygren et al. |
| 4,613,567 A | 9/1986 | Yasoshima et al. |
| 4,626,674 A | 12/1986 | Oinoue |
| 4,643,968 A | 2/1987 | Weaver |
| 4,655,595 A | 4/1987 | Bjork et al. |
| 4,657,543 A | 4/1987 | Langer et al. |
| 4,661,913 A | 4/1987 | Wu et al. |
| 4,663,296 A | 5/1987 | Revillet et al. |
| 4,693,884 A | 9/1987 | Kleiner et al. |
| 4,693,972 A | 9/1987 | Mansour et al. |
| 4,713,441 A | 12/1987 | Heller et al. |
| 4,716,123 A | 12/1987 | Wood |
| 4,752,567 A | 6/1988 | De Brabander et al. |
| 4,764,342 A | 8/1988 | Kelln et al. |
| 4,772,484 A | 9/1988 | Kitchell et al. |
| 4,778,758 A | 10/1988 | Ericsson et al. |
| 4,805,623 A | 2/1989 | Jobsis |
| 4,814,144 A | 3/1989 | Edelmann et al. |
| 4,857,313 A | 8/1989 | Song et al. |
| 4,876,208 A | 10/1989 | Gustafson et al. |
| 4,882,168 A | 11/1989 | Casey et al. |
| 4,885,077 A | 12/1989 | Karakelle et al. |
| 4,933,147 A | 6/1990 | Hollar et al. |
| 4,959,301 A | 9/1990 | Weaver et al. |
| 5,002,792 A | 3/1991 | Vegoe |
| RE33,581 E | 4/1991 | Nicoli et al. |
| 5,017,009 A | 5/1991 | Schutt et al. |
| 5,066,465 A | 11/1991 | Kano et al. |
| 5,079,144 A | 1/1992 | Carr et al. |
| 5,079,172 A | 1/1992 | Hari et al. |
| 5,082,630 A | 1/1992 | Partin et al. |
| 5,089,606 A | 2/1992 | Cole et al. |
| 5,149,543 A | 9/1992 | Cohen et al. |
| 5,173,164 A | 12/1992 | Egen et al. |
| 5,196,527 A | 3/1993 | Ookuma et al. |
| 5,208,037 A | 5/1993 | Wright et al. |
| 5,218,039 A | 6/1993 | Stoy et al. |
| 5,239,170 A | 8/1993 | Hughlett |
| 5,240,618 A | 8/1993 | Caldwell et al. |
| 5,288,611 A | 2/1994 | Kohne |
| 5,314,805 A | 5/1994 | Haugland et al. |
| 5,329,461 A | 7/1994 | Allen et al. |
| 5,350,697 A | 9/1994 | Swope et al. |
| 5,405,783 A | 4/1995 | Pirrung et al. |
| 5,466,416 A | 11/1995 | Ghaed et al. |
| 5,468,606 A | 11/1995 | Bogart et al. |
| 5,488,567 A | 1/1996 | Allen et al. |
| 5,491,097 A | 2/1996 | Ribi et al. |
| 5,494,829 A | 2/1996 | Sandstrom et al. |
| 5,496,701 A | 3/1996 | Pollard-Knight |
| 5,556,764 A | 9/1996 | Sizto et al. |
| 5,578,460 A | 11/1996 | Ebersole et al. |
| 5,599,668 A | 2/1997 | Stimpson et al. |
| 5,604,099 A | 2/1997 | Erlich et al. |
| 5,622,868 A | 4/1997 | Clarke et al. |
| 5,623,707 A | 4/1997 | Kusaka |
| 5,648,652 A | 7/1997 | Sekiya et al. |
| 5,656,432 A | 8/1997 | Claverys et al. |
| 5,792,622 A | 8/1998 | Botsford |
| 5,824,494 A | 10/1998 | Feldberg |
| 5,828,716 A | 10/1998 | Bisconte de Saint Julien |
| 5,843,651 A | 12/1998 | Stimpson et al. |
| 5,849,486 A | 12/1998 | Heller et al. |
| 5,863,754 A | 1/1999 | Bajard |
| 5,866,345 A | 2/1999 | Wilding et al. |
| 5,872,013 A | 2/1999 | Leunissen et al. |
| 5,888,760 A | 3/1999 | Godsey et al. |
| 5,922,593 A | 7/1999 | Livingston |
| 5,939,291 A | 8/1999 | Loewy et al. |
| 5,958,704 A | 9/1999 | Starzl et al. |
| 5,976,821 A | 11/1999 | Huston et al. |
| 5,981,268 A | 11/1999 | Kovacs et al. |
| 5,993,634 A | 11/1999 | Simpson et al. |
| 6,017,696 A | 1/2000 | Heller |
| 6,043,048 A | 3/2000 | Johnston et al. |
| 6,051,380 A | 4/2000 | Sosnowski et al. |
| 6,054,270 A | 4/2000 | Southern |
| 6,086,824 A | 7/2000 | Fanning et al. |

(56) References Cited

U.S. PATENT DOCUMENTS

| | | |
|---|---|---|
| 6,096,272 A | 8/2000 | Clark et al. |
| 6,099,803 A | 8/2000 | Ackley et al. |
| 6,101,946 A | 8/2000 | Martinsky |
| 6,103,479 A | 8/2000 | Taylor |
| 6,107,054 A | 8/2000 | Gibbs |
| 6,122,599 A | 9/2000 | Mehta |
| 6,136,171 A | 10/2000 | Frazier et al. |
| 6,143,247 A | 11/2000 | Sheppard, Jr. et al. |
| 6,153,400 A | 11/2000 | Matsumura et al. |
| 6,153,416 A | 11/2000 | Yuan |
| 6,169,394 B1 | 1/2001 | Frazier et al. |
| 6,176,620 B1 | 1/2001 | Obara |
| 6,214,560 B1 | 4/2001 | Yguerabide et al. |
| 6,221,592 B1 | 4/2001 | Schwartz et al. |
| 6,241,894 B1 | 6/2001 | Briggs et al. |
| 6,242,188 B1 | 6/2001 | Dattagupta et al. |
| 6,245,508 B1 | 6/2001 | Heller et al. |
| 6,251,615 B1 | 6/2001 | Oberhardt |
| 6,251,616 B1 | 6/2001 | Barbera-Guillem et al. |
| 6,251,624 B1 | 6/2001 | Matsumura et al. |
| 6,264,825 B1 | 7/2001 | Blackburn et al. |
| 6,270,953 B1 | 8/2001 | Malcus-Vocanson et al. |
| 6,274,384 B1 | 8/2001 | Starzl et al. |
| 6,290,839 B1 | 9/2001 | Kayyem et al. |
| 6,372,895 B1 | 4/2002 | Bentsen et al. |
| 6,379,897 B1 | 4/2002 | Weidenhammer et al. |
| 6,391,264 B2 | 5/2002 | Hammer et al. |
| 6,391,546 B1 | 5/2002 | Karube et al. |
| 6,391,577 B1 | 5/2002 | Mikkelsen et al. |
| 6,391,937 B1 | 5/2002 | Beuhler et al. |
| 6,395,506 B1 | 5/2002 | Pitner et al. |
| 6,403,367 B1 | 6/2002 | Cheng et al. |
| 6,416,969 B2 | 7/2002 | Matsumura et al. |
| 6,432,694 B1 | 8/2002 | Malmqvist |
| 6,437,551 B1 | 8/2002 | Krulevitch et al. |
| 6,472,166 B1 | 10/2002 | Wardlaw et al. |
| 6,472,228 B2 | 10/2002 | Wang et al. |
| 6,548,263 B1 | 4/2003 | Kapur et al. |
| 6,551,841 B1 | 4/2003 | Wilding et al. |
| 6,573,088 B2 | 6/2003 | Gemmell et al. |
| 6,596,532 B1 | 7/2003 | Hyman et al. |
| 6,605,453 B2 | 8/2003 | Ozkan et al. |
| 6,607,888 B2 | 8/2003 | Schwartz et al. |
| 6,611,765 B2 | 8/2003 | Boeufgras et al. |
| 6,642,682 B1 | 11/2003 | Perkins et al. |
| 6,703,819 B2 | 3/2004 | Gascoyne |
| 6,716,620 B2 | 4/2004 | Bashir et al. |
| 6,809,862 B2 | 10/2004 | Behnsen et al. |
| 6,841,379 B2 | 1/2005 | Matson |
| 6,844,028 B2 | 1/2005 | Mao et al. |
| 6,872,545 B2 | 3/2005 | Griner et al. |
| 6,900,030 B2 | 5/2005 | Pitner et al. |
| 6,951,714 B2 | 10/2005 | Giovannoni et al. |
| 7,067,194 B2 | 6/2006 | Mao et al. |
| 7,108,775 B2 | 9/2006 | Bahatt et al. |
| 7,115,384 B2 | 10/2006 | Clark et al. |
| 7,123,345 B2 | 10/2006 | Sugihara et al. |
| 7,214,299 B2 | 5/2007 | Armstrong |
| 7,250,775 B1 | 7/2007 | Collins et al. |
| 7,258,837 B2 | 8/2007 | Yager et al. |
| 7,306,924 B2 | 12/2007 | Gomez et al. |
| 7,341,841 B2 | 3/2008 | Metzger et al. |
| 7,348,183 B2 | 3/2008 | Fritsch et al. |
| 7,397,540 B2 | 7/2008 | Lundgren et al. |
| 7,413,891 B2 | 8/2008 | Bashir et al. |
| 7,429,355 B2 | 9/2008 | Bishop et al. |
| 7,435,579 B2 | 10/2008 | Bashir et al. |
| 7,451,646 B2 | 11/2008 | Cleland et al. |
| 7,481,977 B2 | 1/2009 | Percival et al. |
| 7,510,637 B2 | 3/2009 | Barlow et al. |
| 7,561,789 B2 | 7/2009 | Border et al. |
| 7,564,245 B2 | 7/2009 | Lee |
| 7,576,307 B2 | 8/2009 | Yazdanfar et al. |
| 7,601,300 B2 | 10/2009 | Blanton et al. |
| 7,622,078 B2 | 11/2009 | Pagés Pinyol |
| 7,629,029 B2 | 12/2009 | Mao et al. |
| 7,642,068 B2 | 1/2010 | Steiner et al. |
| 7,651,837 B2 | 1/2010 | Ohno et al. |
| 7,670,793 B2 | 3/2010 | Glencross |
| 7,678,256 B2 | 3/2010 | Davalos et al. |
| 7,687,239 B2 | 3/2010 | Goldberg et al. |
| 7,689,022 B2 | 3/2010 | Weiner et al. |
| 7,723,095 B2 | 5/2010 | Cleuziat et al. |
| 7,754,148 B2 | 7/2010 | Yu et al. |
| 7,842,504 B2 | 11/2010 | Devlin, Sr. |
| 7,873,268 B2 | 1/2011 | Segawa et al. |
| 7,901,624 B2 | 3/2011 | Hansen et al. |
| 7,910,062 B2 | 3/2011 | Yu et al. |
| 7,955,555 B2 | 6/2011 | Blecka et al. |
| 8,014,583 B2 | 9/2011 | Zahniser |
| 8,029,746 B2 | 10/2011 | Yu et al. |
| 8,058,078 B2 | 11/2011 | Hansen et al. |
| 8,071,319 B2 | 12/2011 | Metzger et al. |
| 8,102,276 B2 | 1/2012 | Sugiura |
| 8,168,443 B2 | 5/2012 | Yu et al. |
| 8,178,602 B2 | 5/2012 | Mao et al. |
| 8,188,438 B2 | 5/2012 | Li |
| 8,304,245 B2 | 11/2012 | Kuypers et al. |
| 8,323,466 B2 | 12/2012 | Kim et al. |
| 8,329,437 B1 | 12/2012 | Ayliffe |
| 8,335,393 B2 | 12/2012 | Kotani |
| 8,354,307 B2 | 1/2013 | Lee |
| 8,361,298 B2 | 1/2013 | Sabin et al. |
| 8,361,299 B2 | 1/2013 | Sabin et al. |
| 8,364,409 B2 | 1/2013 | Rieder et al. |
| 8,368,964 B2 | 2/2013 | Xu et al. |
| 8,372,353 B2 | 2/2013 | Lee et al. |
| 8,372,600 B2 | 2/2013 | Sachs et al. |
| 8,391,582 B2 | 3/2013 | Weiner et al. |
| 8,421,484 B2 | 4/2013 | Prodan et al. |
| 8,460,887 B2 | 6/2013 | Goldberg et al. |
| 8,478,445 B2 | 7/2013 | Hansen et al. |
| 8,481,281 B2 | 7/2013 | Demirev et al. |
| 8,508,652 B2 | 8/2013 | Albu et al. |
| 8,512,636 B2 | 8/2013 | Blanton et al. |
| 8,513,001 B2 | 8/2013 | Weiss et al. |
| 8,563,298 B2 | 10/2013 | Lowery, Jr. et al. |
| 8,603,769 B2 | 12/2013 | Feng et al. |
| 8,614,056 B2 | 12/2013 | Davis et al. |
| 8,635,028 B2 | 1/2014 | Sengupta et al. |
| 8,647,835 B2 | 2/2014 | Walsh et al. |
| 8,652,800 B2 | 2/2014 | Walsh et al. |
| 8,703,061 B2 | 4/2014 | Guzman |
| 8,709,344 B2 | 4/2014 | Bishop et al. |
| 8,765,062 B2 | 7/2014 | Linder et al. |
| 8,779,779 B2 | 7/2014 | Wang et al. |
| 8,780,181 B2 | 7/2014 | Olesen et al. |
| 8,804,105 B2 | 8/2014 | Ayliffe |
| 8,821,814 B2 | 9/2014 | Cho et al. |
| 8,828,680 B2 | 9/2014 | Williams et al. |
| 8,841,118 B2 | 9/2014 | Robinson et al. |
| 8,895,255 B1 | 11/2014 | Goldberg et al. |
| 8,911,987 B2 | 12/2014 | Robinson et al. |
| 8,932,523 B2 | 1/2015 | Linder et al. |
| 8,943,588 B1 | 1/2015 | Speegle et al. |
| 8,969,072 B2 | 3/2015 | Robinson et al. |
| 8,970,826 B2 | 3/2015 | Liu et al. |
| 9,007,233 B2 | 4/2015 | Sugiura |
| 9,048,771 B2 | 6/2015 | Ohba et al. |
| 9,057,714 B2 | 6/2015 | Gomm et al. |
| 9,090,462 B2 | 7/2015 | Straus |
| 9,133,498 B2 | 9/2015 | Kwon et al. |
| 9,150,900 B2 | 10/2015 | Bishop et al. |
| 9,213,043 B2 | 12/2015 | Cook et al. |
| 9,248,422 B2 | 2/2016 | Ching et al. |
| 9,274,132 B2 | 3/2016 | Wilson et al. |
| 9,290,382 B2 | 3/2016 | Straus |
| 9,353,396 B2 | 5/2016 | Demirev et al. |
| 9,405,288 B2 | 8/2016 | Ogata |
| 9,434,937 B2 * | 9/2016 | Metzger ............... C12M 47/12 |
| 9,567,621 B2 | 2/2017 | Robinson et al. |
| 2001/0009774 A1 | 7/2001 | Shin et al. |
| 2001/0053535 A1 | 12/2001 | Bashir et al. |
| 2002/0028519 A1 | 3/2002 | Yguerabide et al. |

(56) References Cited

U.S. PATENT DOCUMENTS

| | | |
|---|---|---|
| 2002/0031795 A1 | 3/2002 | James et al. |
| 2002/0119455 A1 | 8/2002 | Chan |
| 2002/0127144 A1 | 9/2002 | Mehta |
| 2002/0148729 A1 | 10/2002 | Armstrong |
| 2002/0155490 A1 | 10/2002 | Skinner et al. |
| 2002/0155591 A1 | 10/2002 | Farina et al. |
| 2002/0164677 A1 | 11/2002 | Giovannoni et al. |
| 2003/0023149 A1 | 1/2003 | Montemagno et al. |
| 2003/0032171 A1 | 2/2003 | Gemmell et al. |
| 2003/0032173 A1 | 2/2003 | Farina et al. |
| 2003/0036054 A1 | 2/2003 | Ladisch et al. |
| 2003/0119028 A1 | 6/2003 | Graves et al. |
| 2003/0124623 A1 | 7/2003 | Yager et al. |
| 2003/0134269 A1 | 7/2003 | Hairai et al. |
| 2003/0147132 A1 | 8/2003 | Behnsen et al. |
| 2003/0153023 A1 | 8/2003 | Starzl et al. |
| 2003/0157587 A1 | 8/2003 | Gomez et al. |
| 2003/0170613 A1 | 9/2003 | Straus |
| 2003/0186341 A1 | 10/2003 | Kuhn et al. |
| 2003/0211566 A1 | 11/2003 | Gazenko |
| 2003/0224436 A1 | 12/2003 | Nelson et al. |
| 2004/0052426 A1 | 3/2004 | Landesman |
| 2004/0089546 A1 | 5/2004 | Bahatt et al. |
| 2004/0168916 A1 | 9/2004 | Fuchs et al. |
| 2004/0189311 A1 | 9/2004 | Glezer et al. |
| 2005/0048599 A1 | 3/2005 | Goldberg et al. |
| 2005/0059105 A1 | 3/2005 | Alocija et al. |
| 2005/0112544 A1 | 5/2005 | Xu et al. |
| 2005/0114041 A1 | 5/2005 | Gawad et al. |
| 2005/0118705 A1 | 6/2005 | Rabbitt et al. |
| 2005/0121596 A1 | 6/2005 | Kam et al. |
| 2005/0202523 A1 | 9/2005 | Shaw et al. |
| 2005/0208592 A1 | 9/2005 | Caron et al. |
| 2005/0238652 A1 | 10/2005 | Tsuji et al. |
| 2005/0255445 A1 | 11/2005 | Van Damme et al. |
| 2006/0120916 A1 | 6/2006 | Kolari et al. |
| 2006/0141618 A1 | 6/2006 | Yasuda et al. |
| 2006/0166184 A1 | 7/2006 | Yasuda et al. |
| 2006/0194307 A1 | 8/2006 | Yasuda et al. |
| 2006/0243594 A1 | 11/2006 | Schnelle et al. |
| 2007/0037225 A1 | 2/2007 | Metzger et al. |
| 2007/0238146 A1 | 10/2007 | Tyler et al. |
| 2007/0298513 A1 | 12/2007 | Starzl et al. |
| 2008/0014181 A1 | 1/2008 | Ariff et al. |
| 2008/0046286 A1 | 2/2008 | Halsted |
| 2008/0072664 A1 | 3/2008 | Hansen et al. |
| 2008/0138799 A1 | 6/2008 | Cheng et al. |
| 2008/0193965 A1 | 8/2008 | Zeng et al. |
| 2008/0221805 A1 | 9/2008 | Andrews |
| 2008/0241858 A1 | 10/2008 | Metzger et al. |
| 2009/0012723 A1 | 1/2009 | Treado et al. |
| 2009/0051372 A1 | 2/2009 | Sethu et al. |
| 2009/0104689 A1 | 4/2009 | Kim et al. |
| 2009/0203063 A1 | 8/2009 | Wheeler et al. |
| 2009/0208072 A1 | 8/2009 | Seibel et al. |
| 2010/0048428 A1 | 2/2010 | Coyer et al. |
| 2010/0075340 A1 | 3/2010 | Javanmard |
| 2010/0099139 A1 | 4/2010 | Ben-David et al. |
| 2010/0120016 A1 | 5/2010 | Li et al. |
| 2010/0129858 A1 | 5/2010 | Walsh et al. |
| 2010/0248281 A1 | 9/2010 | Straus |
| 2010/0267165 A1 | 10/2010 | Bruls et al. |
| 2011/0023690 A1 | 2/2011 | Wilson |
| 2011/0117577 A1 | 5/2011 | Reboud et al. |
| 2011/0136165 A1 | 6/2011 | Vojnovic et al. |
| 2011/0183856 A1 | 7/2011 | Agan et al. |
| 2011/0237446 A1 | 9/2011 | Treado et al. |
| 2011/0256617 A1 | 10/2011 | Cocchi et al. |
| 2012/0028342 A1 | 2/2012 | Ismagilov et al. |
| 2012/0077206 A1 | 3/2012 | Metzger et al. |
| 2012/0103817 A1 | 5/2012 | Omori et al. |
| 2012/0105837 A1 | 5/2012 | Ingber |
| 2012/0142032 A1 | 6/2012 | Morgan |
| 2012/0149584 A1 | 6/2012 | Olle |
| 2012/0169863 A1 | 7/2012 | Bachelet et al. |
| 2012/0223217 A1 | 9/2012 | Zheng et al. |
| 2012/0244519 A1 | 9/2012 | Olesen et al. |
| 2012/0258874 A1 | 10/2012 | Narain et al. |
| 2013/0017534 A1 | 1/2013 | Nickel et al. |
| 2013/0045878 A1 | 2/2013 | McCue |
| 2013/0089886 A1 | 4/2013 | Feng et al. |
| 2013/0183694 A1 | 7/2013 | Janetzko et al. |
| 2013/0217063 A1 | 8/2013 | Metzger et al. |
| 2013/0271060 A1 | 10/2013 | Messersmith et al. |
| 2013/0295588 A1 | 11/2013 | Watkins et al. |
| 2013/0295597 A1 | 11/2013 | DeWitte et al. |
| 2013/0324437 A1 | 12/2013 | Pogliano et al. |
| 2013/0345525 A1 | 12/2013 | Kline |
| 2014/0038171 A1 | 2/2014 | Metzger et al. |
| 2014/0179726 A1 | 6/2014 | Bajaj et al. |
| 2014/0199719 A1 | 7/2014 | Shih et al. |
| 2014/0278136 A1 | 9/2014 | Shamsheyeva et al. |
| 2014/0278143 A1 | 9/2014 | Garstecki et al. |
| 2014/0323340 A1 | 10/2014 | Goldberg et al. |
| 2014/0343868 A1 | 11/2014 | Colwell et al. |
| 2015/0225762 A1 | 8/2015 | Metzger et al. |
| 2015/0293270 A1 | 10/2015 | Jarvius et al. |
| 2015/0301002 A1 | 10/2015 | DeWitte et al. |
| 2015/0337351 A1 | 11/2015 | Metzger |
| 2016/0010138 A1 | 1/2016 | Shamsheyeva et al. |
| 2016/0051985 A1 | 2/2016 | Knight et al. |
| 2016/0238826 A1 | 8/2016 | Shields et al. |
| 2016/0279633 A1 | 9/2016 | Bachelet et al. |
| 2016/0348091 A1 | 12/2016 | Metzger et al. |
| 2017/0029864 A1 | 2/2017 | Straus |

FOREIGN PATENT DOCUMENTS

| | | |
|---|---|---|
| EP | 1648286 | 4/2006 |
| EP | 2 645 108 A1 | 10/2013 |
| EP | 2 987 851 A1 | 2/2016 |
| EP | 2507663 B1 | 2/2017 |
| GB | 1520733 | 8/1978 |
| JP | 52102491 | 8/1977 |
| JP | 58198759 | 11/1983 |
| JP | H11505405 | 5/1999 |
| JP | 2001509008 | 7/2001 |
| JP | 2002500892 | 1/2002 |
| JP | 2002502597 | 1/2002 |
| JP | 2002330799 | 11/2002 |
| JP | 2003527601 | 9/2003 |
| JP | 200481019 | 3/2004 |
| JP | 2004513628 | 5/2004 |
| WO | WO 8901162 | 2/1989 |
| WO | WO 9011525 | 10/1990 |
| WO | WO 9104491 | 4/1991 |
| WO | WO 9313197 | 7/1993 |
| WO | WO 9402831 | 2/1994 |
| WO | WO 9411728 | 5/1994 |
| WO | WO 9508640 | 3/1995 |
| WO | WO 9528641 | 10/1995 |
| WO | WO 9614431 | 5/1996 |
| WO | WO 9822618 | 5/1998 |
| WO | WO 9822808 | 5/1998 |
| WO | WO 9840741 | 9/1998 |
| WO | WO 9920789 | 4/1999 |
| WO | WO 9937799 | 7/1999 |
| WO | WO 9940174 | 8/1999 |
| WO | WO 9958948 | 11/1999 |
| WO | WO 0024941 | 5/2000 |
| WO | WO 0131332 | 5/2001 |
| WO | WO 0169230 | 9/2001 |
| WO | WO 0238724 | 5/2002 |
| WO | WO 02088299 | 11/2002 |
| WO | WO 03012525 A1 | 2/2003 |
| WO | WO 03022999 | 3/2003 |
| WO | WO 03025208 | 3/2003 |
| WO | WO 03048736 | 6/2003 |
| WO | WO 03065009 | 8/2003 |
| WO | WO 03073100 | 9/2003 |
| WO | WO 2005027714 | 3/2005 |
| WO | WO 2006/015374 A2 | 2/2006 |
| WO | WO 2006028601 A2 | 3/2006 |
| WO | WO 2006066216 | 6/2006 |

(56) References Cited

FOREIGN PATENT DOCUMENTS

| WO | WO 2006135904 | 12/2006 |
| WO | WO 2009124068 | 10/2009 |
| WO | WO 2010/062350 A1 | 6/2010 |
| WO | WO 2010/062352 A1 | 6/2010 |
| WO | WO 2012122314 | 9/2012 |
| WO | WO 2012/162133 A1 | 11/2012 |
| WO | WO 2013/072069 A1 | 5/2013 |
| WO | WO 2014040088 | 3/2014 |
| WO | WO 2014100456 | 6/2014 |
| WO | WO 2014145899 | 9/2014 |
| WO | WO 2014153194 | 9/2014 |
| WO | WO 2014169921 A1 | 10/2014 |
| WO | WO2016207065 A1 | 12/2016 |

OTHER PUBLICATIONS

Burnham C-1358: Poster—"Rapid Detection of *Klebsiella pneumoniae* Carbapenemase (KPC) Producing Isolates Using the BACcel™ Digital Microscopy System," Presented at ASM 2013 May 18, 2013, Denver, CO.

Burnham et al., "Rapid Ertapenem Susceptibility Testing and *Klebsiella pneumoniae* Carbapenemase (KPC) Phenotype Detection in *Klebsiella pneumoniae* Using Automated Microscopy of Immobilized Live Bacterial Cells," *J Clin Microbiol.*, Jan. 3, 2014.

Cooper et al. D-4013: Poster—"Potential Impact of Rapid Phenotype Identification on Antimicrobial Prescribing," Presented at the 48th ICAAC and IDSA Oct. 28, 2008, Washington, DC.

Douglas et al. Poster—"Rapid Microbiological Identification and Major Drug Resistance Phenotyping with Novel Multiplexed Automated Digital Microscopy (MADM) for Ventilator-Associated Pneumonia (VAP) Surveillance," Presented at ATS 2011 May 16, 2011, Denver, CO.

Douglas et al., Rapid Automated Microscopy for Microbiological Surveillance of Ventilator-associated Pneumonia, *Am J Respir Crit Care Med.* 191:566-573, 2015.

Gamage et al. 2556: Poster—"Rapid Detection of Clinically Important *Staphylococcus aureus* Resistance Phenotypes Directly from Positive Blood Cultures Using Automated Microscopy," Presented at ASM2014 May 20, 2014, Boston, MA.

Hance et al. K-392: Poster—"Rapid Identification of Live *Acinetobacter* spp. in Bronchoalveolar Lavage Specimens by Automated Immunofluorescence Microscopy," Presented at the 47th ICAAC Sep. 27, 2007.

Hance et al. C-065: Poster—"A Rapid Indirect Enzyme-Linked Immunosorbent Assay for Identification of *Acinetobacter* spp. from Cultured Isolates," Presented at the American Society for Microbiology 108th General Meeting Jun. 2, 2008.

Hance et al. P0539: Poster—"Pathogen Identification from Positive Blood Cultures Using Automated Sample Preparation and Automated Fluorescent in situ Hybridization (FISH)," Presented at ECCMID 2014, May 11, 2014, Barcelona, Spain.

Hance et al. Poster 2032: Poster—"Rapid Bacterial Identification Directly from Positive Blood Cultures Using Automated Sample Preparation and Multiplexed Fluorescence in situ Hybridization (FISH)," ASM2014, Boston, MA May 20, 2014.

Lisby et al. ePoster "Performance of the new Accelerate ID/AST System in Highly Resistant *Acinetobacter baumannii* Bloodstream Infection Isolates, Compared to Routine Laboratory Testing," ECCMID Apr. 23, 2015, Copenhagen, Denmark.

Metzger et al. C-163: Poster—"Direct Observation of Inducible Clindamycin Resistance in *Staphylococcus aureus* Using Single Live Cell Imaging," Presented at the American Society for Microbiology General Meeting May 23, 2006.

Metzger C-032: Poster—"Direct Identification of Methicillin Resistant *Staphylococcus aureus* (MRSA) Using Small Numbers of Immobilized Cells and Response to Oxacillin (OCA) by Automated Growth Analysis," Presented at the American Society for Microbiology 107th General Meeting, May 22, 2007.

Metzger et al. D-892: Poster—"Identification of mecA in *Staphylococcus aureus* Using Small Numbers of Immobilized Cells and the Response to Cefoxitin (FOX) by Automated Growth Analysis," Presented at the 47th ICAAC Sep. 28, 2007.

Metzger et al. C-005: Poster—"Direct Identification of MRSA and $MLS_B$ Phenotypes in *Staphylococcus aureus* Using Small Numbers of Immobilized Cells," Presented at the American Society for Microbiology 108th General Meeting Jun. 2, 2008.

Metzger et al. C-145: Poster—"Direct Detection and Enumeration of Viable Bacteria in Human Bronchoalveolar Lavage Specimens Using Automated Growth Rate Analysis," Presented at the American Society for Microbiology 108th General Meeting Jun. 2, 2008.

Metzger et al. D-282: Poster—"Direct Identification of the ESBL Phenotype in *Enterobacteriaceae* Isolates Using Small Numbers of Immobilized Cells," Presented at the 48th ICAAC and IDSA Oct. 25, 2008, Washington, DC.

Metzger et al. C-207: Poster—"Rapid Identification of Resistance Phenotypes in Gram-Negative Bacilli Using Automated Digital Microscopy," Presented at the 109th General Meeting of the ASM, Philadelphia, PA, May 23, 2009.

Metzger et al. C-1140: Poster—"Rapid Quantitation and Identification of *Pseudomonas aeruginosa, Staphylococcus aureus*, and *Acinetobacter baumannii* in Bronchoalveolar Lavage Fluid," Presented at the 110th General Meeting of the ASM May 24, 2010, San Diego, CA.

Metzger et al. Poster: "Same-Day ID and Resistance Phenotyping Directly from Respiratory Specimens by Automated Microscopy," Presented at ASM 2011, New Orleans, May 22, 2011.

Metzger et al. Poster—"Automated 4-Hour Detection of Heteroresistant Vancomycin-Intermediate *Staphylococcus aureus* (hVISA)," Presented at ASM 2011 May 22, 2011, New Orleans.

Metzger et al. D-791: Poster—"Direct-From-Remnant-Specimen Quantitative Identification Using Automated Microscopy," Presented at the 50th ICAAC, Sep. 13, 2010, Boston, MA.

Metzger and Dunne D-102: Poster—"Same-Shift ID Directly from Respiratory Specimens by Automated Microscopy," Presented at 51st ICAAC Sep. 17, 2011, Chicago, IL.

Metzger et al. C-157: Poster—"3-Hour ESBL Detection from Positive Blood Cultures Using Multiplexed Automated Digital Microscopy (MADM)," Presented at ASM 2012 Jun. 17, 2012, San Francisco, CA.

Metzger et al. C-751: Poster—"Rapid and Automated Specimen Preparation for Clinical Microbiology," Presented at ASM 2012 Jun. 17, 2012, San Francisco, CA.

Metzger D-1410: Poster—"Same-Day Blood Culture with Digital Microscopy," Presented at ICAAC 2012 Sep. 11, 2012, San Francisco, CA.

Metzger et al., "Rapid Simultaneous Identification and Quantitation of *Staphylococcus aureus* and *Pseudomonas aeruginosa* Directly from Bronchoalveolar Lavage Specimens Using Automated Microscopy," *Diagn Microbiol Infect Dis.* 79:160-165, 2014. *Diagn Microbiol Infect Dis.* Epublished Dec. 7, 2013.

Price et al., "Rapid Antibiotic Susceptibility Phenotypic Characterization of *Staphylococcus aureus* Using Automated Microscopy of Small Numbers of Cells," *J Microbiol Methods.* 98:50-58, 2014.

Price et al. ePoster—"Rapid Identification and Antimicrobial Susceptibility Testing of Bacteria in Bloodstream Infections Using the Accelerate ID/AST Technology," ECCMID Apr. 23, 2015, Copenhagen, Denmark.

Rajagopal et al., "Eight Gram-Negative Bacteria are 10,000 Times More Sensitive to Cationic Detergents than to Anionic Detergents," *Can J Microbiol.* 49:775-779, 2003.

Shamsheyeva et al. 2538: Poster—"Rapid Antimicrobial Susceptibility Testing of Non-Fermenting Gram-Negative Bacilli Directly from Positive Blood Cultures by Automated Microscopy," Presented at ASM2014, May 20, 2014, Boston, MA.

Shamsheyeva et al. 2555: Poster—"Evaluation of an Antimicrobial Susceptibility Testing Algorithm to Determine Minimum Inhibitory Concentration Using Growth of Immobilized *Staphylococcal* Cells Measured by Automated Microscopy," Presented at ASM2014, May 20, 2014, Boston, MA.

Shamsheyeva et al. D-873: Poster "Evaluation of an Antimicrobial Susceptibility Testing Algorithm for Gram-Positive Bacteria

(56) References Cited

OTHER PUBLICATIONS

Directly from Positive Blood Culture Using Automated Microscopy Analysis of Susceptibility Patterns," Presented at ICAAC Sep. 7, 2014, Washington, DC.
Shamsheyeva et al. P0332: Poster—"Next Generation Automated Phenotypic Antibiotic Susceptibility Testing Utilizing Automated Microscopy Analysis of Bacterial Cells," Presented at ECCMID 2014 May 10, 2014, Barcelona, Spain.
Shamsheyeva et al. P0335: Poster—"5-Hour Antibiotic Susceptibility Testing of *Enterococcus faecium* and *E. faecalis*, and *Acinetobacter baumannii* Directly from Positive Blood Cultures Using Automated Microscopy," Presented at ECCMID 2014 May 10, 2014, Barcelona, Spain.
Wallace et al. D-918: Poster—"Rapid Identification of Gram-negative Bacteria in Positive Blood Culture Broth Using a Multiplex Fluorescence in situ Hybridization (FISH) Assay and Automated Microscopy," Presented at ICAAC Sep. 7, 2014, Washington, DC.
Zierdt et al., "Lysis-Filtration Blood Culture Versus Conventional Blood Culture in a Bacteremic Rabbit Model," *J Clin Microbiol.* 15:74-77, 1982.
European Partial Supplementary Search Report for EP 13835702.5 mailed on Feb. 25, 2016 (8 pages).
Iregui et al., "Clinical Importance of Delays in the Initiation of Appropriate Antibiotic Treatment for Ventilator-Associated Pneumonia," *Chest* 122:262-268, 2002.
Kumar et al., "Duration of Hypotension Before Initiation of Effective Antimicrobial Therapy is the Critical Determinant of Survival in Human Septic Shock," *Crit Care Med.* 34:1589-1596, 2006.
Luna et al., "Appropriateness and Delay to Initiate Therapy in Ventilator-Associated Pneumonia," *Eur Respir J.* 27:158-164, 2006.
van Soestbergen and Lee, "Pour Plates or Steak Plates?," *Appl Microbiol.* 18:1092-1093, 1969.
Accelerate Diagnostics: "Fast Phenotypic Antibiotic Susceptibility Testing: Connie Price, M.D.," YouTube, Aug. 28, 2015, pp. 1-6, XP054976622, Retrieved from the Internet: URL:https://www.youtube.com/watch?v=1n1GW54atXE&index=3 &list=PLsmqpsknnk2_ENp8Xd3BhK0vu9nfU0p6y [retrieved on Jun. 22, 2016].
Accelerate Diagnostics: "Accelerate ID/AST," Vimeo, May 18, 2015, pp. 1-6, XP054976621, Retrieved from the Internet: URL:https://vimeo.com/128112270 [retrieved on Jun. 22, 2016].
Mohamad et al., "Bacteria Identification from Microscopic Morphology Using Naïve Bayes," *IJCSEIT* 4:1-9, 2014.
RMM Product Matrix, http://rapidmicromethods.com/files/matrix.php, accessed Jul. 27, 2016. (13 pages).
PCT/US2016/025075 Invitation to Pay Additional Fees with Partial International Search mailed on Jul. 6, 2016 (8 pages).
EPO; Application No. EP 13835702.5, European Supplementary Search Report mailed on Jun. 24, 2016 (12 pages).
EPO; Application No. EP 13835702.5, Rules 70(2) and 70a(2) EPC Communication mailed on Jul. 12, 2016, 2016 (1 page).
Choi et al., "Rapid Antibiotic Susceptibility Testing by Tracking Single Cell Growth in a Microfluidic Agarose Channel System," *Lab Chip* 13:280-287, 2013.
EP 14762411.8 Partial Supplementary European Search Report mailed on Jul. 29, 2016 (10 pages).
Isse et al., "Digital Transplantation Pathology: Combining Whole Slide Imaging, Multiplex Staining and Automated Image Analysis," *Am J Transplant.* 12:27-37, 2012.
Unknown, "Bacterial Counts—Quantitative Analysis of Microbes," Biology 251 General Microbiology Lab, Jul. 30, 2013, pp. 1-5, retrieved from internet: URL:http://biolabs.tmee.edu/Micro%20Web/BacterialCounts.pdf [retrieved on Oct. 21, 2016].
EP 14762411.8 Extended European Search Report mailed on Nov. 7, 2016 (11 pages).
PCT/US2016/025075, International Search Report and Written Opinion mailed Nov. 15, 2016 (36 pages).
Levin-Reisman et al., "Automated Imagining With ScanLag Regeals Previously Undetectable Bacterial Growth Phenotypes," *Nature Methods* 7:737-739, 2010.
Tokuda et al., "Optical and Electric Multifunctional CMOS Image Sensors for on-Chip Biosensing Applications," *Materials* 4:84-102, 2011.
EP16200084.8 Partial European Search Report dated Mar. 1, 2017.
Alere, Inc., "Adult Isolator Tube Solution Material Safety Data Sheet," (2010).
Aminian et al., "A Conformal Bayesian Network for Classification of Mycobacterium Tuberculosis Complex Lineages," BMC Bioinformatics, 11(Suppl 3): S4 (2010).
Anzaldi et al., "Overcoming the Heme Paradox: Herne Toxicity and Tolerance in Bacterial Pathogens," Immun. 78(12): 4977-4989 (2010).
Ateya et al., "Volume Cytometry: Microfluidic Sensor for High-Throughput Screening in Real Time," Analytical Chem., 77:1290-1294, (2005).
Atlas and Snyder, Handbook of Media for Clinical Microbiology, 2006. CRC press.
Bae et al., "Immunosensor for Detection of Yersinia Enterocolitica Based on Imaging Ellipsometry," Analytical Chem., 76:1799-1803, (2004).
Balaban et al., "Bacterial Persistence as a Phenotypic Switch," Science, 305:1622-1625, (2004).
Barton et al., "Measurement of Bacterial Growth Rates on Polymers," J. Biomed. Mater Res., 32:271-278, (1996).
Bayoudh et al., "Electrical Detection and Characterization of Bacterial Adhesion Using Electrochemical Impedance Spectroscopy-Based Flow Chamber," Colloids and Surfaces A: Physicochem. Eng. Aspects, 318, pp. 291-300, (2008).
Beaglehole, "Performance of a Microscopic Imaging Ellipsometer," Rev. Sci. Instrum., 59:12, pp. 2557-2559, (1988).
Belding et al., "Effect of Sodium Polyanetholesulfonate on Antimicrobial Systems in Blood," Appl. Microbiol. 24(5): 691-698 (1972).
Benecky et al., "Simultaneous Detection of Multiple Analytes Using Copalis Technology: A Reduction to Practice," Clin. Chem., 44:9, pp. 2052-2054, (1998).
Boehm et al., "On-Chip Microfluidic Biosensor for Bacterial Detection and Identification," Sensors and Actuators, 126, pp. 508-514, (2007).
Bridson, E.Y., and Gould, G.W., "Quantal Microbiology," Lett. Appl. Microbiology, 30:95-98, (2000).
Cabrera et al., "Continuous Concentration of Bacteria in a Microfluidic Flow Cell Using Electrokinetic Techniques," Electrophoresis 22:355-362, 2001.
Chan et al., "Evaluation of Lysis Filtration as an Adjunct to Conventional Blood Culture," J. Clin. Pathol. 39:89-92 (1986).
Cheung et al., "Microfluidic Impedance-Based Flow Cytometry," Cytometry A, 77A, pp. 648-666, (2010).
Dai et al., "Electrokinetic Trapping and Concentration Enrichment of DNA in a Microfluidic Channel," J. Am. Chem. Soc., 125:13026-13027, (2003).
Daims et al., "Quantification of Uncultured Microorganisms by Fluorescence Microscopy and Digital Image Analysis," Appl. Microbiol. Biotechnol., 75:237-248, (2007).
De Brabander et al., "Detection of Gold Probes With Video-Enhanced Contrast Microscopy: Nanovid Microscopy," Amer. J., 185, pp. 282-295, (1989).
Delehanty and Ligler, "A Microarray Immunoassay for Simultaneous Detection of Proteins and Bacteria," Anal. Chem., 74, pp. 5681-5687, (2002).
Desai and Armstrong, "Separation, Identification, and Characterization of Microorganisms by Capillary Electrophoresis," Microbiology and Molecular Biology Reviews, 67:38-51, (2003).
Dorn et al., "Blood Culture Technique Based on Centrifugation: Developmental Phase," J. Clin. Micro. 3(3): 251-257 (1976).
Dwek et al., "Synchronization of Cell Division in Microorganisms by Percoll Gradients," J. Bacteriol. 144(1):17-21 (1980).
Elfwing et al., "Observing Growth and Division of Large Numbers of Individual Bacteria by Image Analysis," Appl. Environ. Micro., 70:675-678, (2004).

(56) References Cited

OTHER PUBLICATIONS

Elghanian et al., "Selective Colorimetric Detection of Polynucleotides Based on the Distance-Dependent Optical Properties of Gold Nanoparticles," Science, 277:1078-1081, (1997).
Ertl et al., "Electrochemical Biosensor Array for the Identification of Microorganisms Based on Lectin-Lipopolysaccharide Recognition," Analytical Chem., 73:4241-4248, (2001).
Ertl et al., "Rapid Identification of Viable *Escherichia coli* Subspecies with Electrochemical Screen-Printed Biosensor Array," Biosensors Bioelectronics, 18:907-916, (2003).
Eun et al., "Encapsulating Bacteria in Agarose Microparticles Using Microfluidics for High-Throughput Cell Analysis and Isolation," ACS Chem. Biol., 18:260-266, (2011).
Fesenko et al, "Biosensing and Monitoring of Cell Populations Using the Hydrogel Bacterial Microchip," Biosens Bioelectron. 20:1860-1865, 2005.
Forero et al., "Automatic Identification Techniques of Tuberculosis Bacteria," Proc. SPIE 5203, Applications of Digital Image Processing XXVI, (Tescher, A.G., Ed.) SPIE Proceedings, 5203:71-81, (2003).
Friedman et al., "Precise Temporal Modulation in the Response of the SOS DNA Repair Network in Individual Bacteria," PLoS Bio. 3:1261-1263, (2005).
Gadkari, "Optimal Hydrogels for Fast and Safe Delivery of Bioactive Compounds," A Thesis Submitted to the Faculty of Drexel University, (2007).
Gao et al., "Epipolarization Microscopic Immunogold Assay: A Combination of Immunogold Silver Staining, ELISA and Epipolarization Microscopy," Biotech. & Histochem., 70:211-216, (1995).
Gast, R.K. et al., "Detection of *Salmonella entertidis* in Incubated Pools of Egg Contents by Fluorescence Polarization and Lateral Flow Immunodiffusion," Poultry Science, 82:687-690, (2003).
Gawad et al., "Micromachined Impedance Spectroscopy Flow Cytometer for Cell Analysis and Particle Sizing," Lab on a Chip, 1:76-82, (2001).
Geerts et al., "Nanovid Microscopy," Nature, 1991, 351:765-766, (1991).
Geesey and White, "Determination of Bacterial Growth and Activity at Solid-Liquid Interfaces," Annu. Rev. Microbiol., 44, pp. 579-602, (1990).
Gomez et al., "Microfluidic Biochip for Impedance Spectroscopy of Biological Species," Biomedical Microdevices, 3:3, pp. 201-209, (2001).
Greef et al., "Identification and Growth Rate Quantitation of Individual Bacterial Clones Using a Novel Microfluidic Concentration Device," Accelr8 Technology Corporation (1 page), 2006.
Hach Company, "Heterotrophic Bacteria, Pour Plate Method," Edition 7 (10 pages), 2012.
Heileman et al., "Dielectric Spectroscopy as a Viable Biosensing Tool for Cell and Tissue Characterization and Analysis," Biosensors and Bioelectronics, 49:348-359, (2013).
Huang et al., "Electric Manipulation of Bioparticles and Macromolecules on Microfabricated Electrodes," Analytical Chem., 73, pp. 1549-1559, (2001).
Huang et al., "Lysozyme for Capture of Microorganisms on Protein Biochips," Enzyme and Microbial. Technol., 33:958-966, (2003).
Inverness Medical Group, "Wampole Isostat Microbial Tubes, Instructions for Use and Supplementary Application Notes," (2008).
Jampachaisri et al., "Classification of oligonucleotide fingerprints: application for microbial community and gene expression analyses," Bioinformatics 21:3122-3130 (2005).
Ji et al., "Real-time Detection of Bacterial Contamination in Dynamic Aqueous Environments Using Optical Sensors," Analytical Chem., 76:1411-1418, (2004).
Jin et al., "A Biosensor Concept Based on Imaging Ellipsometry for Visualization of Biomolecular Interactions," Analytical Biochem., 232, pp. 69-72, (1995).
Kastenholz, B. "Comparison of the Electrochemical Behavior of the High Molecular Mass Cadmium Proteins in Arabidopsis Thaliana and in Vegetable Plants on Using Preparative Native Continuous Polyacrylamide Gel Electrophoresis (PNC-Page)," Electroanalysis 18:103-106 (2006).
Kim and Soh, "Simultaneous Sorting of Multiple Bacterial Targets Using Integrated Dielectrophoretic-Magnetic Activated Cell Sorter," Lab Chip 9:2313-2318, 2009.
Kim et al., "Programmed Trapping of Individual Bacteria Using Micrometre-Size Sieves," Lab on a Chip, 11, pp. 1089-1095, (2011).
Koh et al., "Integrating Polymerase Chain Reaction, Valving, and Electrophoresis in a Plastic Device for Bacterial Detection," Analytical Chem., 75:4591-4598, (2003).
Kremser, et al., "Capillary Electrophoresis of Biological Particles: Viruses, Bacteria, and Eukaryotic Cells," Electrophoresis 25: 2282-2291 (2004).
Kubitschko et al.,"Sensitivity Enhancement of Optical Immunosensors with Nanoparticles," Analytical Biochem., 253:112-122, (1997).
Kuehn et al., "Automated Confocal Laser Scanning Microscopy and Semiautomated Image Processing for Analysis of Biofilms," Appl. Environ. Microbio., 64:4115-4127, (1998).
Lagally et al., "Integrated Portable Genetic Analysis Microsystem for Pathogen/Infectious Disease Detection," Analytical Chem., 76:3162-3170, (2004).
Lawrence et al., "Computer-Enhanced Darkfield Microscopy for the Quantitative Analysis of Bacterial Growth and Behavior on Surfaces," J. Microbial. Methods 10:123-138, (1989).
Lerner, "Bayesian Fluorescence in Situ Hybridisation Signal Classification," Artif. Intell. Med. 30:301-316 (2004).
Liu et al., "CMEIAS: A Computer-Aided System for the Image Analysis of Bacterial Morphotypes in Microbial Communities," Micro. Ecololgy., 41:173-194, (2001).
Lloyd and Hayes, "Vigour, Vitality and Viability of Microorganisms," FEMS Microbio. Lett., 133:1-7, (1995).
Lochhead, "Microfluidic Devices that Capture Bacteria for Growth and Kill Analysis," Nov. 14, 2006, XP055207195, retrieved from the Internet: URL:http://acceleratediagnostics.com/docs/AVS_2006_Capture.pdf [retrieved on Aug. 11, 2015].
Maeyama et al., "Confocal Imaging of Biofilm Formation Process Using Fluoroprobed *Escherichia coli* and Fluorostained Exopolysaccharide," J. Biomed. Mater Res., 70:274-282, (2004).
Magnusdottir et al. "Collection of Capillary Electrophoresis Fractions on a Moving Membrane," From Methods in Molecular Biology, vol. 162: Capillary Electrophoresis of Nucleic Acids, vol. 1: Introduction to the Capillary Electrophoresis of Nucleic Acids. 22: 323-331 (2001).
Markx et al., "Dielectrophoretic Separation of Cells: Continuous Separation," Biotechnol. Bioeng., 45:337-343, (1995).
Markx, G.H. et al., "Dielectrophoretic Characterization and Separation of Micro-Organisms" Microbiology, 140, pp. 585-591 (1994).
Meinders et al., "In Situ Enumeration of Bacterial Adhesion in a Parallel Plate Flow Chamber—Elimination or in Focus Flowing Bacteria From the Analysis," J. Microbiol. Methods, 16:119-124, (1992).
Miller et al., "SOS Response Induction by Beta-Lactams and Bacterial Defense Against Antibiotic Lethality," Science, 305, pp. 1629-1631, (2004).
Mishra et al., "On-Chip Micro-Biosensor for the Detection of Human CD4+ Cells Based on AC Impedance and Optical Analysis," Biosensors and Bioelectronics, 21:696-704, (2005).
Moffitt et al., "The Single-Cell Chemostat: An Agarose-Based, Microfluidic Device for High-Throughput, Single-Cell Studies of Bacteria and Bacterial Communities," Lab Chip 12:1487-1494, 2012.
Molin et al., "Rapid Detection of Bacterial Growth in Blood Cultures by Bioluminescent Assay of Bacterial ATP," J. Clin. Microbiol., 18:521-525 (1983).
Mueller et al., "Issues in Pharmacokinetics and Pharmacodynamics of Anti-Infective Agents: Kill Curves Versus MIC," Antimicrob. Agents Chemother., 48:369-377, (2004).
Oheim, "High-Throughput Microscopy Must Re-Invent the Microscope Rather Than Speed up its Functions," British Journal of Pharmacology, 152:1-4, (2007).

(56) References Cited

OTHER PUBLICATIONS

Okano et al., "Using Microparticle Labeling and Counting for Attomole-Level Detection in Heterogeneous Immunoassay," Analytical Biochem., 202:120-125, (1992).
Orjih, "Heme Polymerase Activity and the Stage Specificity of Antimalarial Action of Chloroquine," J. Pharm. Exp. Ther. 282(1):108-112 (1997).
Ozkan et al., "Electro-Optical Platform for the Manipulation of Live Cells," Langmuir, 19:1532-1538, (2003).
Plowman, "Planar Integrated Optical Methods for Examining Thin Films and Their Surface Adlayers," Biomaterials, 19:341-355, (1998).
Probst et al., "Polydimethylsiloxane Sub-Micron Traps for Single-Cell Analysis of Bacteria," Micromachines, 4:357-369, (2013).
Rabinovitch et al., "Removal and Inactivation of *Staphylococcus epidermidis* Biofilms by Electrolysis," Applied and Environmental Microbiology, 72:6364-6366, (2006).
Rohner et al., "Advantage of Combining Resin with Lytic BACTEC Blood Culture Media," J. Clin. Micro. 35(10):2634-2638 (1997).
Rohner et al., "Evaluation of the New Improved BHI-Lysis Blood Culture Medium for the BCB Roche System," Eur. J. Clin. Micro. Infect. Dis. 10:620-624, 1991.
Rosch et al., "Chemotaxonomic Identification of Single Bacteria by Micro-Raman Spectroscopy: Application to Clean-Room-Relevant Biological Contaminations," Applied and Environmental Microbiology, 71:1626-1637, (2005).
Rose et al., "Using the Membrane Filter in Clinical Microbiology," Med. Lab. 3: 22-23, 29, 43, 1969. Note: The numbered pages omitted from this article are advertisements.
Rowe et al., "Array Biosensor for Simultaneous Identification of Bacterial, Viral, and Protein Analytes," Analytical Chem., 71:3846-3652, (1999).
Salmon et al., "Video-Enhanced Differential Interference Contrast Light Microscopy," BioTechniques, 7:624-633, (1989).
Sapsford et al., "Detection of Campylobacter and *Shigella* species in Food Samples Using an Array Biosensor," Analytical Chem., 76:433-440, (2004).
Schrot et al., "Method for Radiorespirometric Detection of Bacteria in Pure Cultures and in Blood," Appl. Micro. 26(2): 867-873 (1973).
Sippy, et al., "Rapid Electrochemical Detection and Identification of Catalase Positive Micro-Organisms", Biosensors & Bioelectronics, 18:741-749, (2003).
Stewart et al., "Aging and Death in an Organism that Reproduces by Morphologically Symmetric Division," PLoS Biology, 3:295-300 (2005).
Stimpson et al., "Real-Time Detection of DNA Hybridization and Melting on Oligonucleotide Arrays by Using Optical Wave Guides," Genetics, Proc. Natl. Acad. Sci. USA, 92:6379-6383, (1995).
Stuart, "The Value of Liquid for Blood Culture," J. Clin. Path. 1:311-314 (1948).
Sun et al., "Single-Cell Microfluidic Impedance Cytometry: A Review," Microfluidics and Nanofluidics, 8:423-443, (2010).
Suo et al., "Immunoimmobilization of Living *Salmonella* for Fundamental Studies and Biosensor Applications," *Salmonella*—A Diversified Superbug, 25:497-522, (2012).
Taton et al., "Two-Color Labeling of Oligonucleotide Arrays via Size-Selective Scattering of Nanoparticle Probes," J. Am. Chem. Soc., 123, pp. 5164-5165, (2001).
Tison, D.L., "Culture Confirmation of *Escherichia coli* Serotype 0157:H7 by Direct Immunofluorescence," J. Clin. Microbio., 28:612-613, (1990).
Tsang et al., "Characterization of Murine Monoclonal Antibodies Against Serogroup B *Salmonellae* and Application as Serotyping Reagents," J. Clin. Micro., 29:1899-1903, (1991).
van der Borden et al., "Electric Current-Induced Detachment of *Staphylococcus epidermidis* Biofilms from Surgical Stainless Steel, Applied and Environmental Microbiology,"Applied and Environmental Microbiology, 70:6871-6874, (2004).
Varshney et al., "A Label-Free, Microfluidics and Interdigitated Array Microelectrode-Based Impedance Biosensor in Combination with Nanoparticles Immunoseparation for Detection of *Escherichia coli* O157:H7 in Food Samples," Sensors and Actuators, 128:99-107, (2007).
Vega, et al., "Effect of Ionic Strength and Porosity on Ion Diffusion in Agarose Gels," Summer Bioengineering Conference, Sonesta Beach Resort in Key Biscayne, Florida, 1-2 (2003).
Vener et al., "A Novel Approach to Nonradioactive Hybridization Assay of Nucleic Acids Using Stained Latex Particles," Analytical Biochem., 198:308-311, (1991).
Von Haebler et al., "The Action of Sodium Polyanethol Sulphonate ("Liquoid") on Blood Cultures," J. Pathol. Bacteriol. 46(2): 245-252 (1938).
Weeratna et al., "Gene Expression Profiling: From Microarrays to Medicine", J. Clin. Immunol., 24:213-224, (2004).
Willaert, Chapter 12 in Fermentation Microbiology and Biotechnology: Cell Immobilization and its Applications in Biotechnology: Current Trends and Future Prospects, p. 313-368, 2006.
Wit and Busscher, "Application of an Artificial Neural Network in the Enumeration of Yeasts and Bacteria Adhering to Solid Substrata," J. Microbio. Methods, 32:281-290 (1998).
Wu et al., "Microfluidic Continuous Particle / Cell Separation via Electroosmotic-Flow-Tuned Hydrodynamic Spreading," J. Micromech. Microeng., 17:1992-1999, (2007).
Yang et al., "Electrical/ Electrochemical Impedance for Rapid Detection of Foodborne Pathogenic Bacteria," Biotechnology Advances, 26:135-150, (2008).
Yeung et al., "Bayesian Model Averaging: Development of an Improved Multi-Class, Gene Selection and Classification Tool for Microarray Data," Bioinformatics 21:2394-2402 (2005).
Zhou, et al., "Automated Image Analysis for Quantitative Fluorescence in Situ Hybridization with Environmental Samples," App. Environ. Microbio. 73(a):2956-2962 (2007).
Zierdt et al., "Development of a Lysis-Filtration Blood Culture Technique," J. Clin. Micro. 5(1):46-50 (1977).
Zierdt, "Blood-Lysing Solution Nontoxic to Pathogenic Bacteria," J. Clin. Micro., 15(1):172-174 (1982).
Zierdt, "Simplified Lysed-Blood Culture Technique," J. Clin. Micro. 23(3):452-455 (1986).
CIPO; Office Action dated Jan. 27, 2014 in Canadian Application No. 2,532,414.
CIPO; Office Action dated Mar. 26, 2015 in Canadian Application No. 2,532,414.
EPO; European Office Action dated Jul. 10, 2014 in Application No. EP 04809482.
EPO; European Office Action dated Jun. 17, 2010 in Application No. EP 04809482.
EPO; European Office Action dated Mar. 13, 2008 in Application No. EP 04809482.
EPO; European Office Action dated Mar. 3, 2014 in Application No. EP 05854636.7.
EPO; European International Search Report and Written Opinion for PCT/US2015/032290, dated Aug. 24, 2015 (13 pages).
EPO; European Search Report dated Aug. 5, 2004 in Application No. EP 98911454.
EPO; European Search Report dated Feb. 13, 2013 in Application No. EP 05854636.7.
EPO; European Search Report dated Oct. 15, 2007 in Application No. EP 03716230.2.
EPO; Intention to Grant dated May 21, 2015 in Application No. 12754797.
EPO; Supplementary European Search Report dated Oct. 19, 2007 in Application No. EP 04809482.
EPO; Supplementary European Search Report dated Sep. 24, 2014 in Application No. 12754797.
PCT; International Preliminary Examination Report dated Jun. 11, 1999 in Application No. PCT/US1998/04086.
PCT; International Preliminary Report on Patentability dated Mar. 10, 2015 in Application No. PCT/US2013/059104.
PCT; International Preliminary Report on Patentability dated Oct. 30, 2007 in Application No. PCT/US2005/045961.
PCT; International Preliminary Report on Patentability dated Oct. 5, 2010 in Application No. PCT/US2009/038988.

(56) References Cited

OTHER PUBLICATIONS

PCT; International Preliminary Report on Patentability dated Sep. 19, 2013 in Application No. PCT/US2012/028139.
PCT; International Preliminary Report on Patentability dated Sep. 26, 2006 in Application No. PCT/US2004/022025.
PCT; International Search Report and Written Opinion dated Aug. 27, 2014 in Application No. PCT/US2014/30745.
PCT; International Search Report and Written Opinion dated Jan. 10, 2014 in Application No. PCT/US2013/059104.
PCT; International Search Report and Written Opinion dated Jun. 8, 2009 in Application No. PCT/US2009/038988.
PCT; International Search Report dated Aug. 7, 2006 in Application No. PCT/US2004/022025.
PCT; International Search Report dated Jul. 14, 1998 in Application No. PCT/US1998/04086.
PCT; International Search Report dated Jul. 30, 2001 in Application No. PCT/US1999/010917.
PCT; International Search Report dated Jun. 27, 2003 in Application No. PCT/US2003/006086.
PCT; International Search Report dated Oct. 15, 2007 in Application No. PCT/US2005/045961.
PCT; International Search Report dated Sep. 28, 2012 in Application No. PCT/US2012/028139.
PCT; Search Report and Written Opinion dated Sep. 28, 2012 in Application No. PCT/US2012/028139.
PCT; Written Opinion dated Aug. 7, 2006 in Application No. PCT/US2004/022025.
PCT; Written Opinion dated Oct. 15, 2007 in Application No. PCT/US2005/045961.

\* cited by examiner

RAPID CELL PURIFICATION SYSTEMS

CROSS REFERENCE TO RELATED APPLICATIONS

This application is a divisional of U.S. patent application Ser. No. 14/004,145, filed Oct. 16, 2013, which is a U.S. National Phase filing under U.S.C. §371 of PCT/US2012/028139, filed Mar. 7, 2012, and claims priority from U.S. Provisional Patent Application Ser. No. 61/449,824, filed Mar. 7, 2011, all of which are incorporated herein by reference in their entirety.

FIELD

This disclosure relates to methods and systems for purifying cells and/or viruses, particularly microorganisms in a sample, particularly in preparation for diagnostics systems.

BACKGROUND

Diagnostic systems that detect cells and/or viruses are of clinical and diagnostic interest. Detection of cells and/or viruses is often prevented or complicated by the presence of contaminants that interfere with collection or detection of the cells and/or viruses. This may be particularly true for cells or viruses that are adhered or fixed to a solid surface prior to detection.

Additionally, operator variability may adversely impact the quality of specimen. Specimen quality is dependent on patient factors including but not limited to differences between patients, and the presence or absence of various interfering substances. In many cases, the specimen is split and analyzed using various diagnostic tests. Therefore, purifying samples reliably and cost-effectively to remove inhomogeneities helps to improve the likelihood of relevant statistical sampling of cells and/or viruses therein.

SUMMARY

Methods and systems for purifying a microorganism are provided. The sample is added to a well disposed in a medium. A potential is applied across the medium to cause the contaminants to enter one or more walls of the well, while the cells and/or viruses are retained in the well. The cells and/or viruses can be removed from the well, and optionally adhered or fixed to a surface, or detected. In one embodiment, the cells and/or viruses may be retained in the well by embedding in the medium. The medium including the embedded cells and/or viruses may be excised or otherwise removed and transferred to a glass slide or other solid surface. The medium may then be cut or sectioned to correspond to the respective wells. The medium is then dried, Gram stained, and the cells/viruses detected.

BRIEF DESCRIPTION OF THE DRAWINGS

FIG. 2I depicts Gram stained microorganisms that may be detected in accordance with the systems and methods described herein.

DETAILED DESCRIPTION

Described herein are various embodiments of systems and methods for purifying cells and/or viruses in a sample. A sample containing cells and/or viruses is added to a well disposed in a medium. A potential is applied across the medium to cause contaminants to enter the medium through one or more walls of said well which retain the cells and/or viruses in the well. The cells and/or viruses are then removed from the well. The cells and/or viruses may also remain in or on the wall of the well, and/or the wall/well may be excised for further analysis.

The systems and methods described herein may concentrate cells and/or viruses from a low content specimen or sample in the wells, thereby removing or reducing potentially interfering debris and resulting in more readable specimens. For example, the disclosed methods and systems may be used in testing of CSF (cerebro-spinal fluid) specimens or other hypocellular specimens. In such samples, bacterial organisms can be localized in 5×5 field of view capture areas (100× objective magnification) to minimize time-consuming searching during microscopic examination. A system having multiple wells may also be used to support parallel processing of sample aliquots for concurrent analyses by multiple downstream methods.

Figure 1:
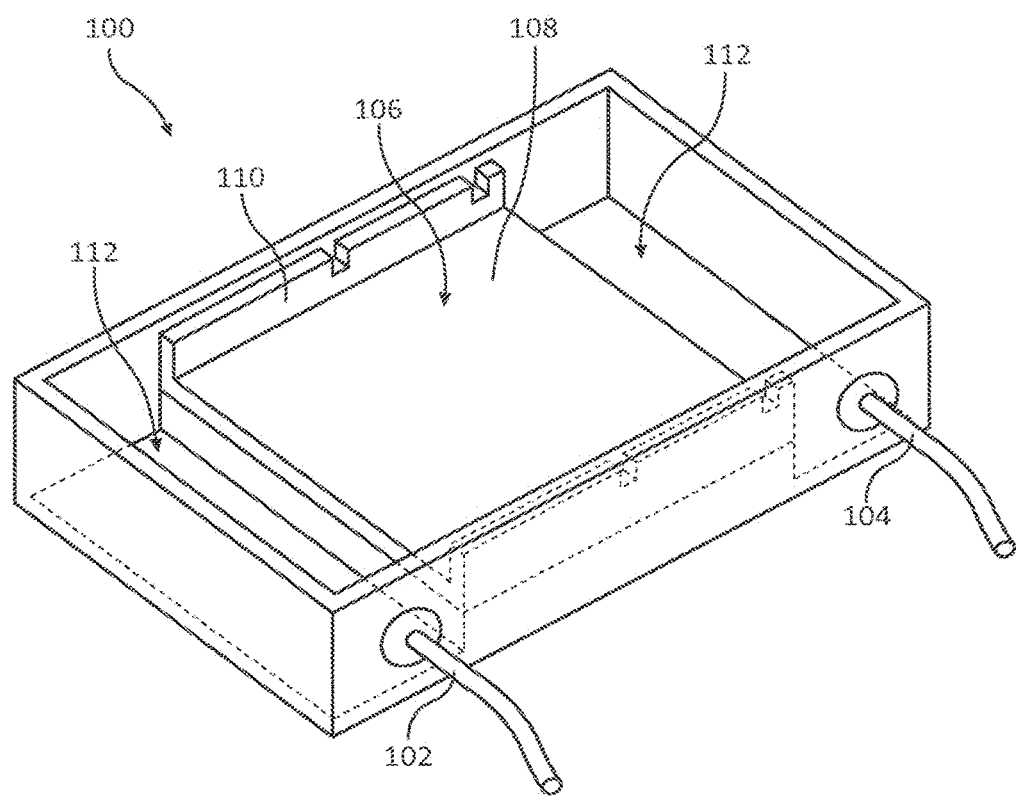
FIG. 1 is a perspective view of an embodiment of a system used to purify a microorganism.

An exemplary embodiment of the system is depicted in FIG. 1. FIG. 1 depicts a system 100 used to purify cells and/or viruses with a cassette 106 configured to receive a medium. The cassette 106 includes a bottom plate 108 and sides 110. Negative electrode 102 and positive electrode 104 are operably connected to the medium through a buffer (not shown) placed in a reservoir 112.

The sample is added to a well disposed in a medium, preferably formed in the medium. In some embodiments, a plastic well may also be disposed in the medium, in addition to well(s) formed in the medium. An electrical potential is applied to the well causing contaminant material to enter the medium while the cells and/or viruses accumulate on the wall of the well. In some embodiments, the cells and/or viruses may be localized on the wall of the well. Cells and/or viruses remain in the well, thereby purifying the sample. The sample may be mixed during or after a time period of the applied electric field. In some embodiments, the process can be repeated until separation of contaminants that interfere with adhesion to a detection surface has been achieved. The well can then be rinsed, and cells and/or viruses recovered. In some embodiments, the wall of the well where the cells and/or viruses have accumulated may be excised or otherwise removed from the rest of the gel medium. Alternatively, the electrical potential can be briefly reversed in polarity to displace the cells and/or viruses from the wall prior to rinsing and recovery. Mixing, applying a potential, and/or reversing polarity of applied field can be performed iteratively to further purify the sample.

In some embodiments, the sample volume recovered is less than, and sometimes substantially less than, the initial sample volume in the wells. In one embodiment, a barrier, such as an impermeable plastic sheet, is inserted into the wells and used to reduce the volume in the wells, thereby further concentrating the cells and/or viruses in the well and providing a reduced sample volume for recovery.

Systems, including electrophoresis boxes and electrodes, can be obtained from Thermo Fisher (Waltham, Mass.) under the EC-Apparatus brand name (e.g., product number EC 250-90).

Figure 2A:
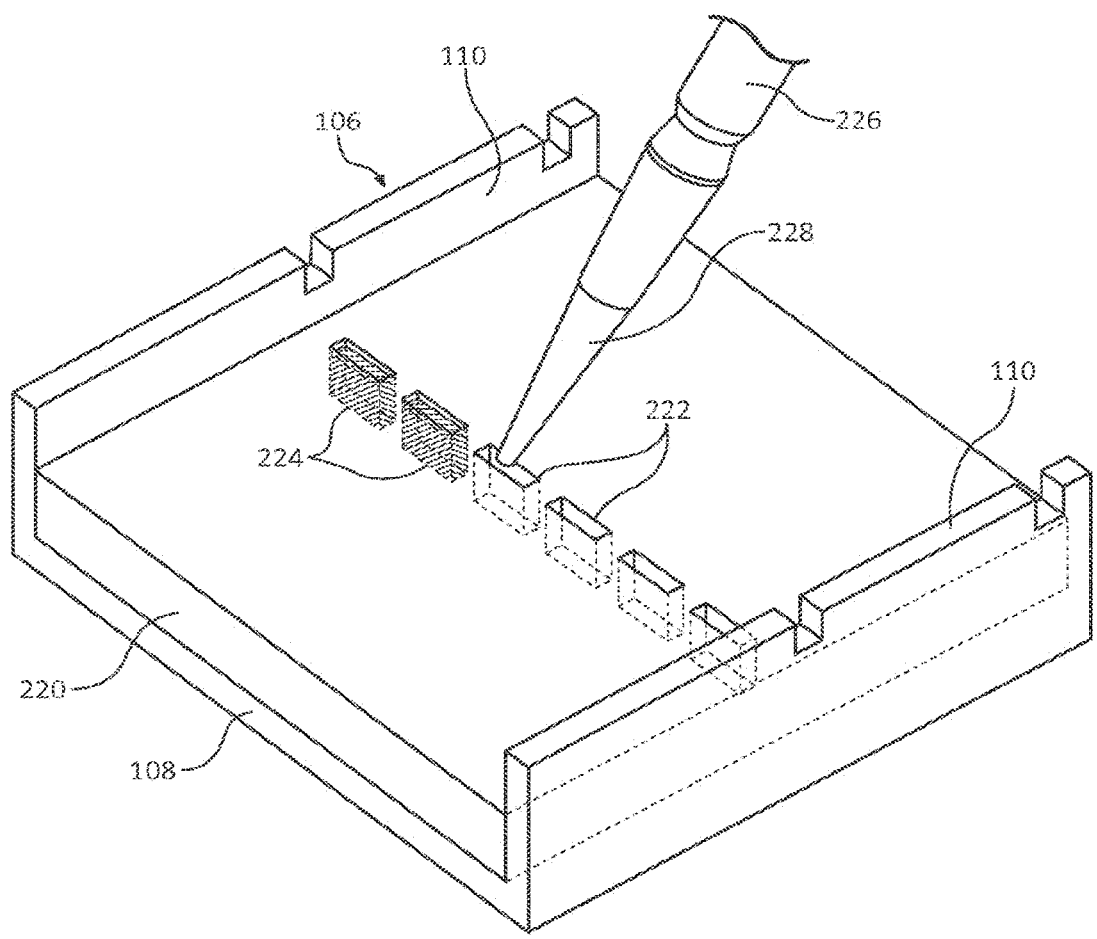
FIG. 2A is a perspective view of an embodiment of a medium in a cassette which may be used with the system of FIG. 1.
Figure 2B:
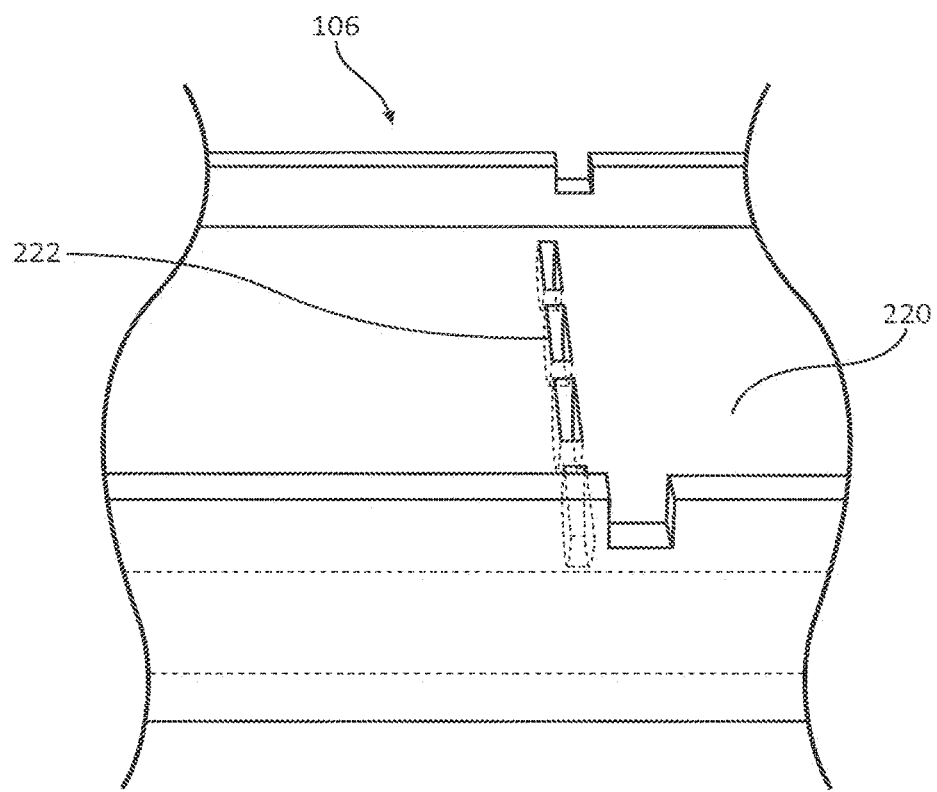
FIG. 2B is a partial perspective view of another embodiment of a medium in a cassette which may be used with the system of FIG. 1.
Figure 2C:
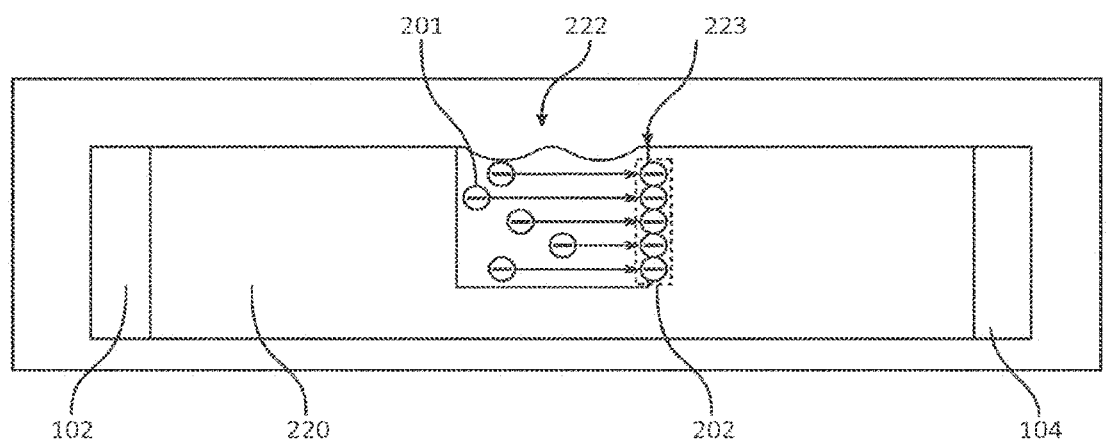
FIG. 2C depicts a side view of the medium and system of FIG. 2B.

FIG. 2A depicts an embodiment of a medium in a cassette 106 comprising a bottom plate 108 and sides 110, which may be used with the system 100. A medium 220 is disposed in the cassette 106 with a plurality of wells 222 in the medium 220. A sample 224 is added in some wells 222 with a pipette 226 comprising a pipette tip 228. Although the medium is shown as a top load gel slab, media in other forms, including but not limited to vertical gel slabs, can be used.

Figure 2D:
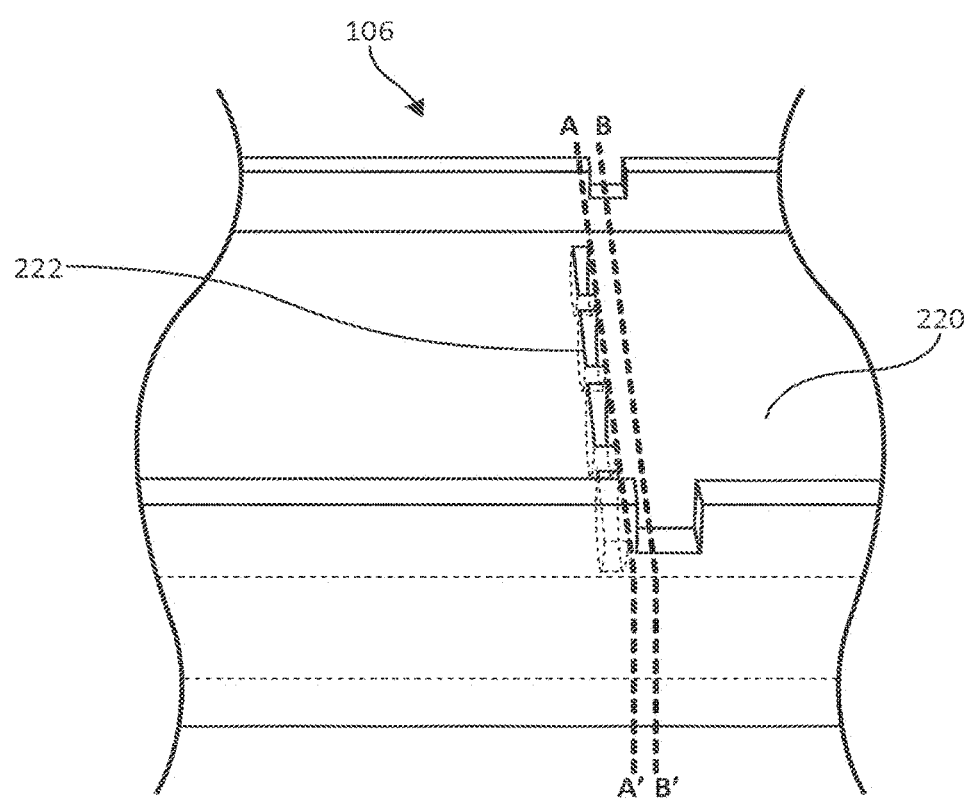
FIGS. 2D and 2E illustrate excision of a portion of the medium of FIG. 2B.
Figure 2E:
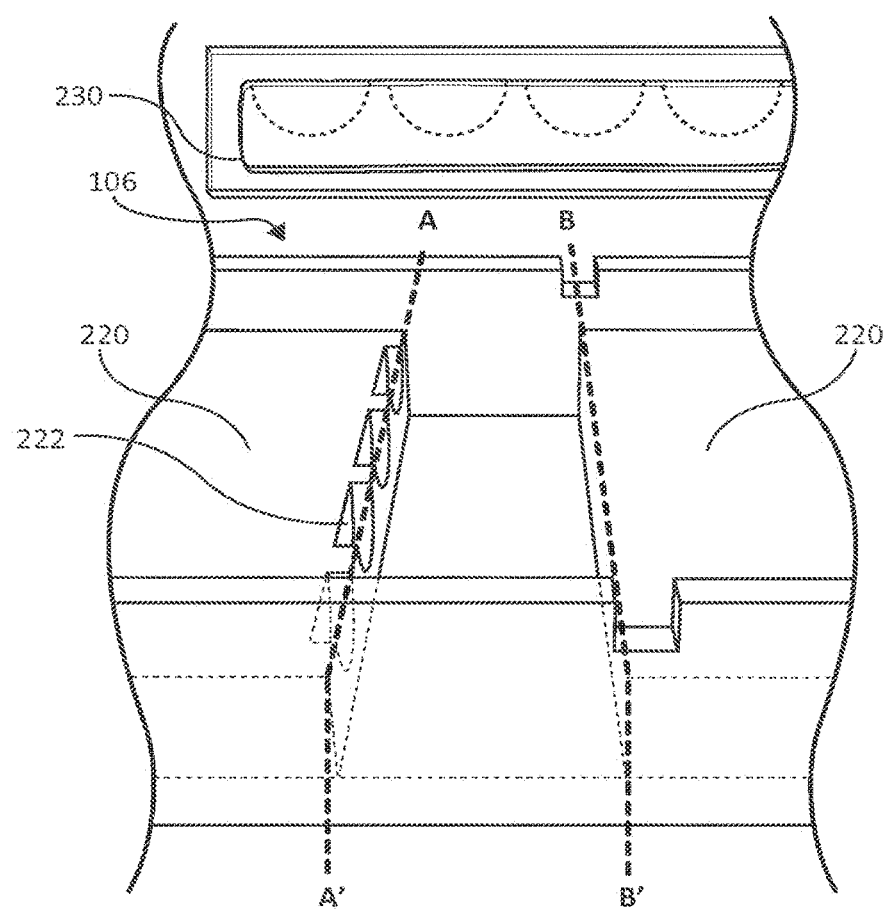

FIGS. 2B-2H illustrate an embodiment where a medium 220 is disposed in a cassette 106 and has a plurality of wells 222 in the medium 220. A sample is added and a potential is applied between negative electrode 102 and positive electrode 104 as described elsewhere herein to cause contaminant material to enter the medium while the cells 201 and/or viruses accumulate or become embedded on the wall 223 of the well 222, depicted in FIG. 2C as concentrated cells 202. As shown in FIGS. 2D-2E, a portion 230 of the medium 220, including at least a portion of the wells 222, is excised, such as by cutting the medium along planes of excision defined by lines A-A' and B-B', or otherwise removed from the medium. In some embodiments, the excision can be robotically automated.

Figure 2F:
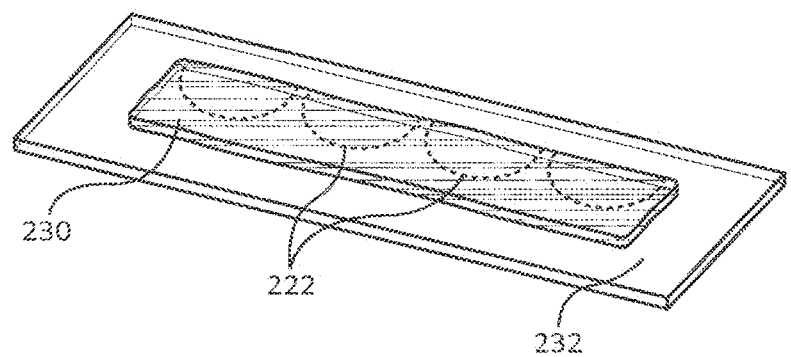
FIGS. 2F, 2G and 2H depict the excised portion of the medium of FIGS. 2D and 2E on a solid surface.
Figure 2G:
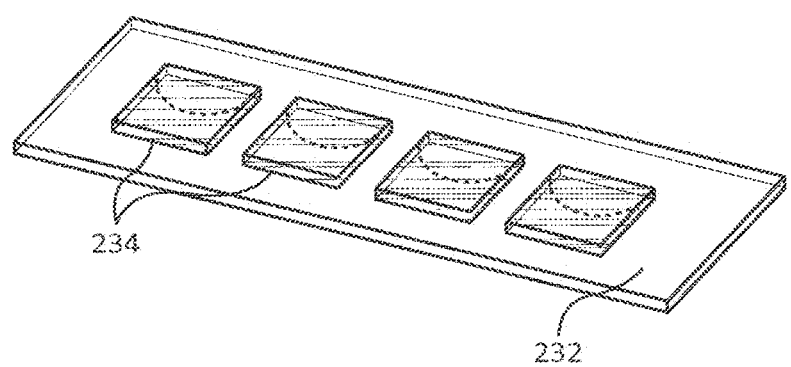
Figure 2H:
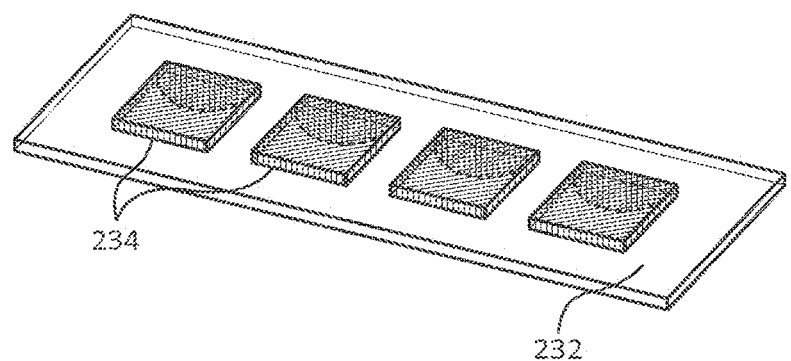
Figure 21:
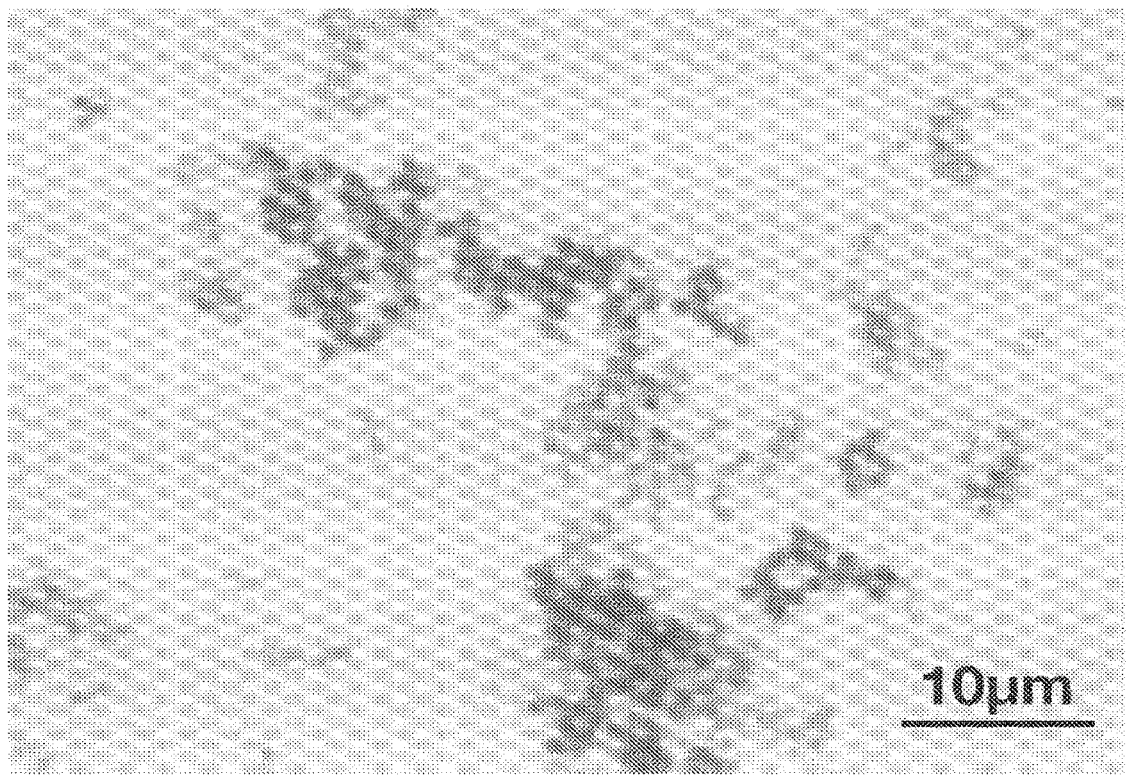

Following excision, the excised portion of the medium may be fixed, for example, for staining or extracting molecular samples for analysis. In some embodiments, and as shown in FIGS. 2F and 2G, the excised portion 230 may be placed on a solid surface 232, such as a glass slide, and the excised portion 230 may be sectioned at each well 222 into sections 231. The sections 231 of excised portion 230 may be dried, Gram stained, and detected as indicated in FIGS. 2H-2I. In some embodiments, a prepared slide (e.g., wherein the sectioned, excised portion has been dried) can be introduced into automated Gram staining equipment.

Figure 2J:
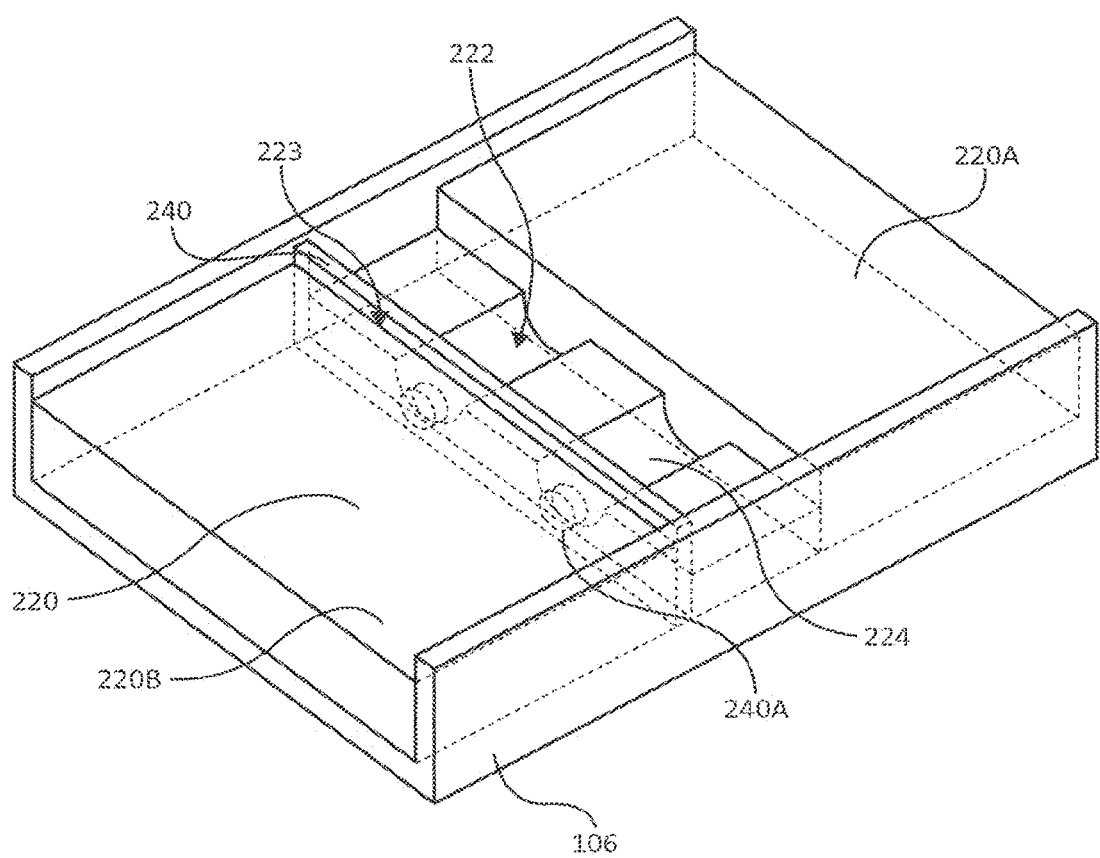
FIG. 2J is a top view of a medium in a cassette which may be used with the system of FIG. 1, wherein a localization device is used to localize the cells and/or viruses.
Figure 2K:
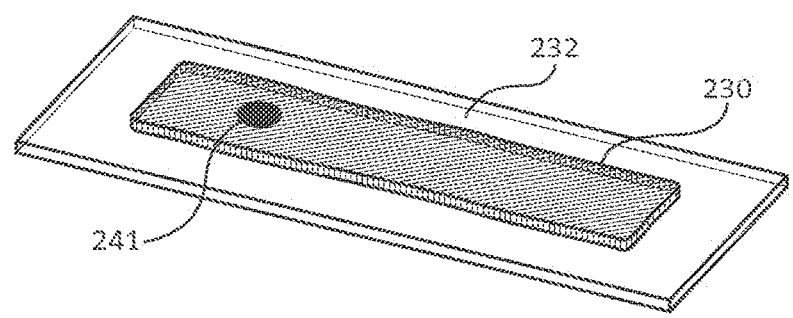
FIG. 2K depicts Gram stained microorganisms that may be detected in accordance with the systems and methods described herein.

In some embodiments, the cells and/or viruses may be localized on the wall of the well by, or with the help of, a localization device. FIGS. 2J and 2K depict an embodiment illustrating a localization device 240 and localized cells 241. FIG. 2J is a top view of a gel medium that utilizes non-conductive materials as a localization device to distort the electric field resulting in localized concentration of cells and/or viruses, such as microorganisms. FIG. 2J illustrates an embodiment where the medium 220 is disposed in the cassette 106 showing a plurality of wells 222, including a plastic well 224, in the medium 220. The medium 220 includes a proximal end 220a and a distal end 220b. Disposed between the wells 222 and the medium 220 is a localization device 240 comprising a non-conductive material including at least one hole or aperture 240a. A sample is added and a potential is applied as described elsewhere herein to cause contaminant material to enter the medium while the cells and/or viruses accumulate or become embedded on the wall 223 of the well 222. In this embodiment, the sample flows through the aperture 240a in the non-conductive localization device 240, thereby localizing the cells and/or viruses that accumulate or become embedded on the wall 223 of the well 222, as described with reference to FIG. 2C. In this embodiment, the non-conductive localization device 240 prevents or inhibits the sample from flowing anywhere but through the aperture(s) 240a. In one embodiment, the non-conductive material may be a plastic film. As described above with reference to FIGS. 2D-2I, a portion of the medium 220, including at least a portion of the wells 222, is excised or otherwise removed. The excised portion 230 may be placed on a solid surface 232, such as a glass slide, and may be dried, Gram stained, and detected. FIG. 2K depicts Gram stained localized microorganisms 241 that have been localized in accordance with the methods and systems described herein.

While FIGS. 2J and 2K depict an embodiment of a system and method for localization using a localization device 240 comprising non-conductive materials, other methods and devices for localization may also be used. In one embodiment, the localization device is a conductive material, such as a metal or metal alloy wire, that is embedded in or placed near a distal end 220b of the medium 220 (i.e., downstream relative to the direction of migration). When a potential is applied, the cells and/or viruses localize on the wall of the well in a location corresponding to the position of the conductive material. That is, where the conductive material is a straight metal wire, the cells and/or viruses localize on the wall of the well in a straight line corresponding to the line of the metal wire. In another embodiment, the localization device includes large and small (or discrete) electrodes are used. For example, a large electrode, such as a sheet electrode, may be placed at a proximal location relative to the proximal end 220a of the medium 220. A small electrode may be placed at a distal location relative to the distal end 220b of the medium 220. When a potential is applied, the cells and/or viruses localize on the wall of the well in a location corresponding to the location of the small electrode. In still other embodiments, the localization device is a discontinuous buffer system. In such a system, the conductivity inside the well is different from the conductivity outside the well. For example, where a well is made of the medium, the conductivity of the sample and the conductivity of the well are different. When a potential is applied, the cells and/or viruses localize on the wall of the well due, at least in part, to this conductivity difference.

Dyes can be used in samples to pre-label or added to provide a tracking dye for purposes of a quantitative reference or sample transfer quality control indicator. Examples of dyes include colorants, bio-active adjuncts such as labeled antibodies, vital stains, mortal stains (such as propidium iodide and the like). Zwitterionic or neutrally charged dye molecules can be used to monitor electro-osmotic flow.

The potential applied across the medium effective for removal of contaminants can be applied for a variable time and is dependent on the sample conductivity. For samples retrieved using normal saline and having a conductivity near that of normal saline, for example, the potential can be applied from 1 to 60 minutes.

In some embodiments, the method includes an asymmetric alternating potential. In other embodiments, the potential is a constant potential. In various embodiments, the applied potential induces electro-osmotic flow that is used to remove contaminants having a neutral charge. The potential can be reversed in polarity to displace cells and/or viruses from the surface of the medium. In some embodiments, the method includes applying a tangential flow across the medium to remove non-permeable contaminants from the surface of the medium. The tangential flow may be applied by flowing the sample over the medium. The tangential flow may be generated using additional buffer that is not the sample. The flow can be continuously cycled over the medium.

When a sample is taken from a patient, there are various components in the sample. For example, in a patient suffering from pneumonia, a sample may include saline, anionic and cationic species, pulmonary surfactants, bacteria, mucus, blood, host cells such as white blood cells, and/or lung tissue cells. Mucus components include, but are not limited to, mucoidal glycoproteins, proteins, extra-cellular nucleic acids, F-actin, lysed white blood cell fragments. Blood components may include, but are not limited to, red cells, white cells, platelets, and plasma. Plasma components may include, but are not limited to, sugar, fat, protein and salt solution, platelets, blood clotting factors, sugars, lipids, vitamins, minerals, hormones, enzymes, antibodies, and other proteins including heme, albumins, immunoglobulins, fibrinogens, regulatory proteins, lipoproteins (chylomicrons, VLDL, LDL, HDL), transferrin, prothrombin, enzymes, proenzymes, residual antibiotics used to treat the patient, and hormones. Lung tissue components include host epithelial cells (intact or lysed). The cells in the alveolar walls of the lung produce and secrete pulmonary surfactant. Pulmonary surfactant is a mixture of phospholipids and proteins. White blood cells may also be present in lung samples. All the above components may be solubilized.

In some embodiments, the cells include blood cells, fungal cells, bacterial cells, or microorganisms including parasites. Examples of blood cells include red blood cells and white blood cells. In some variations, the white blood cells can be neutrophils.

In various embodiments, microorganisms can include bacteria, fungi, algae, and protozoa. In one aspect, the microorganisms are bacteria. The microorganisms can be pathogenic to humans and animals. Suitable microorganisms include any of those well established in the medical art and those novel pathogens and variants that emerge from time to time. Examples of currently known bacteria include, but are not limited to, genera such as *Bacillus, Vibrio, Escherichia, Shigella, Salmonella, Mycobacterium, Clostridium, Cornyebacterium, Streptococcus, Staphylococcus, Haemophilus, Neissena, Yersinia, Pseudomonas, Chlamydia, Bordetella, Treponema, Stenotrophomonas, Acinetobacter, Enterobacter, Klebsiella, Proteus, Serratia, Citrobacter, Enterococcus, Legionella, Mycoplasma, Chlamydophila, Moraxella, Morganella*, and other human pathogens encountered in medical practice. Included in the genera are various species. For example, *Klebsiella* includes, but is not limited to, *Klebsiella pneumoniae, Klebsiella ozaenae, Klebsiella rhinoscleromatis, Klebsiella oxytoca, Klebsiella planticola, Klebsiella terrigena*, and *Klebsiella ornithinolytica*. Examples of viruses include viroids.

Similarly, microorganisms may comprise fungi selected from genera such as *Candida, Aspergillus*, and other human pathogens encountered in medical practice. Viruses can be, but are not limited to, orthomyxoviruses (e.g., influenza virus), paramyxoviruses (e.g., respiratory syncytial virus, mumps virus, measles virus), adenoviruses, rhinoviruses, coronaviruses, reoviruses, togaviruses (e.g., rubella virus), parvoviruses, poxviruses (e.g., variola virus, vaccinia virus), enteroviruses (e.g., poliovirus, coxsackievirus), hepatitis viruses (including hepatitis A, B, and C), herpesviruses (e.g., Herpes simplex virus, varicella-zoster virus, cytomegalovirus, Epstein-B an virus), rotaviruses, Norwalk viruses, hantavirus, arenavirus, rhabdovirus (e.g., rabies virus), retroviruses (including HIV, HTLVI and II), papovaviruses (e.g., papillomavirus), polyomaviruses, picornaviruses, and the like.

The methods and systems described herein can be used to identify host cells harboring viruses. The cells are first purified, and subsequently the cells are manipulated to either produce viruses, or to identify nucleic acids in the cells.

The sample can be obtained from any number of sources, including, but not limited to, bodily fluids (including, but not limited to, blood, urine, serum, lymph, saliva, anal and vaginal secretions, perspiration, peritoneal fluid, pleural fluid, effusions, ascites, and purulent secretions, lavage fluids, drained fluids, brush cytology specimens, biopsy tissue, explanted medical devices, infected catheters, pus, biofilms and semen) of virtually any organism, including mammalian samples and human samples, as well as environmental samples (including, but not limited to, air, agricultural, water and soil samples). In addition, samples can be taken from food processing, which can include both input samples (e.g., grains, milk or animal carcasses), samples in intermediate steps of processing, as well as finished food ready for the consumer. The method can be used for veterinary applications. The methods can be also used for the analysis of milk in the diagnosis and treatment of mastitis, and the analysis of respiratory samples for the diagnosis of bovine respiratory disease. Furthermore, the methods provide for the rapid detection of the presence of potential biological warfare agents in a sample.

Samples can range from less than a milliliter to up to a liter for certain respiratory lavage fluids, and can further range in bacterial concentration from less than one bacterium to greater than $10^9$ bacteria per milliliter. Furthermore, the sample can be present in blood, urine, sputum, lavage fluid or other medium. The sample can be concentrated prior to using the described methods for purifying cells and/or viruses from the sample. Sample concentration both concentrates the sample so that bacteria that are present in small numbers can all be effectively introduced into the system and adequately sampled, as well as so the background liquid medium can be normalized, or in some cases eliminated or reduced, to have consistent properties upon introduction to the system. Sample concentration can be performed by centrifugation, combining samples, removing solvents, and the like. It should be noted, however, that certain samples provided in the description can be used without concentration or other modification.

The rapid detection of various cells and/or viruses is useful for a patient suffering from various diseases and disorders. For example, pneumonia can result from a variety of causes, including infection with bacteria, viruses, fungi, or parasites, as well as chemical or physical injury to the lungs. However, some samples of cells and/or viruses contain contaminants that interfere with their detection. Purification of a microorganism (or virus or other cell), and detection of the type and amount of a microorganism (or virus or other cell) present in a sample, are helpful to diagnose and treat a patient effectively.

In other embodiments, the cells are selectively lysed. For example in the case of intracellular targets, the mammalian cells can be lysed, releasing intracellular microorganisms prior to, during, or after the purification described herein.

Contaminants

Contaminants are removed from the sample into the medium. Contaminants that can be removed include ionic species, including, but not limited to, mono or divalent cations and anions, released intracellular materials, phospholipids, extracellular proteins, mucins, pulmonary surfactants, mucus plugs, pus, glycoproteins, and nucleic acids. Removing contaminants avoids other time intensive preparation steps such as vortexing and centrifugation. In various aspects, the removed contaminants interfere with cells and/or virus surface immobilization, detection, and imaging. Cells and/or viruses remain in the well, and can be recovered. In certain aspects of the purification methods, certain components, such as cellular membrane fragments and larger cellular fragments, are not removed from the sample.

Medium

Organogels, xerogels, and aerogels may also be utilized as the medium. Aerogels include, but are not limited to, silica aerogel, carbon aerogels, alumina, cadmium, and selenide aerogels. Organic aerogels, such as SEAgel, are made of agar. Aerogels made of chalcogens such as sulfur, selenium, and other elements may also be of utility.

In various embodiments, the medium is a hydrogel. In some embodiments, hydrogels are a network of polymer chains that are hydrophilic. Hydrogels can be highly absorbent natural or synthetic polymers, and in some instances can contain over 99% water. In general, hydrogels are solid, yet porous media.

The concentration of the hydrogel affects the migration speed of the contaminants through the hydrogel. Increasing the concentration of the hydrogel decreases the pore size within the hydrogel. Additionally, contaminants with smaller molecules move faster and migrate further than contaminants with larger molecules.

The charge of the hydrogel also affects the migration speed of the contaminants through the hydrogel. Each contaminant molecule migrates to the electrode that carries a charge opposite of that of the contaminant molecule. Most biological materials have a net negative surface charge. Some have a net positive charge if the material has an excess of amines or other positively-charge moieties exposed to the surface. The charge is considered neutral if it is a balance of positive and negative, or uncharged, such as complexes coated with neutral materials that envelope and screen charged materials within. The uncharged material will migrate in the direction of electro-osmotic flow, if present.

The pH of the hydrogel also affects the migration speed of the contaminants and the targets. In some embodiments, the pH is selected to enhance mobility of the contaminants relative to the cells and/or viruses. In some embodiments, a pH may be selected such that the cells and/or viruses are substantially near the isoelectric point, minimizing the cells' and/or viruses' mobility relative to the contaminants. In other embodiments, the pH may be selected to be substantially different from the isoelectric point such that the direction of the cells' and/or viruses' mobility is reversed relative to the contaminants.

In some embodiments, a medium contains nutrients that promote the viability of the cells and/or viruses.

Media used in the systems described can separate contaminant molecules based on both their size and their charge.

The hydrogel's porosity is directly related to the concentration of agarose in the medium. Various levels of effective viscosity can be selected, depending on the experimental objectives.

Examples of hydrogels are alginates, as disclosed in Gadkari, 2007, "Optimal hydrogels for fast and safe delivery of bioactive compounds", Thesis of Drexel University; ethyl-vinyl-acetate copolymer as disclosed in U.S. Pat. No. 3,854,480; esters of hydantoic acid as disclosed in U.S. Pat. No. 3,792,081, olefin saturated polyester 500-8000, polyethylene glycol (PEG) 200-1500, ethyl-vinyl-acetate copolymer 20-40% VA (20-30K), chlorinated polyethylene 25-45% Cl— (20-30K), ethyl-ethylacrylate copolymer 20-40% EA (20-30K), and ethylene vinyl chloride copolymer 25-45% Cl— (20-30K) as disclosed in U.S. Pat. No. 3,938,515; methyl-methacrylate copolymer and glyceryl-methyacrylate copolymer as disclosed in U.S. Pat. No. 3,957,362; ethylene-vinyl-actetate copolymer 4-80% VA (20-30K) as disclosed in U.S. Pat. No. 4,069,307; polysiloxanes as disclosed in U.S. Pat. No. 4,136,250; hydrophilic dihydroxyalkyl acrylate and insoluble copolymer as disclosed in U.S. Pat. No. 4,267,295; cellulose triacetate as disclosed in U.S. Pat. No. 4,220,152; acrylamide, vinylpyrrolidone, and polyethyleneoxide diol as disclosed in U.S. Pat. No. 4,423,099; poly-amino acid homopolymers and copolymers as disclosed in U.S. Pat. No. 4,351,337; polyglutamic acid ethyl-glutamate copolymer (5-50% GA, 80-500 KDa) as disclosed in U.S. Pat. No. 4,450,150; polyoxyethlyene-polyoxypropylene copolymer thermoset as disclosed in U.S. Pat. No. 4,478,822; vinyl cross-linked copolymers of insoluble and soluble monoolefinic esters as disclosed in U.S. Pat. No. 4,548,990; copolymers with N-vinyl-2-pyrrolidone and methacrylates as disclosed in U.S. Pat. No. 4,693,884; polyanhydride as disclosed in U.S. Pat. No. 4,657,543; colpolymer of poly(alkylene oxide) and cyclic ester of alpha hydroxy acid (glycolide) as disclosed in U.S. Pat. No. 4,882,168; polyacrylonitrile-nitric acid copolymer as disclosed in U.S. Pat. No. 5,218,039; N-morpholinoethyl methacrylate and 2-hydroxyethyl methacrylate copolymer as disclosed in U.S. Pat. No. 4,857,313; cross-linked copolymers of vinyl pyrrolidone and allylamine as disclosed in U.S. Pat. No. 4,772,484; water soluble polyacetals having molecular weights from about 5,000-30,000 as disclosed in U.S. Pat. No. 4,713,441; thermoplastic hydrogels of polyvinyl pyrrolidone (PVP) and polyvinyl acetate (PVA), and gelatin as disclosed in U.S. Pat. No. 5,002,792; alginic acid with Ca++, Ba++ or Zn++, pectic acid with Ca++, Ba++ or Zn++, hyaluronic acid with Ca++, Ba++ or Zn++, polyglucuronic acid with Ca++, Ba++ or Zn++, polymanuronic acid with Ca++, Ba++ or Zn++, polygalacturonic acid with Ca++, Ba++ or Zn++, polyarabinic acid with Ca++, Ba++ or Zn++, and kappa-carrageenan with Ca++, Ba++ or Zn++, as disclosed in U.S. Pat. No. 5,089,606; charged side-chain polyphosphazenes with Ca++ cross-linking as disclosed in U.S. Pat. No. 5,149,543; carboxymethylcellulose as disclosed in U.S. Pat. No. 5,208,037; agarose as disclosed in U.S. Pat. No. 3,961,628; polyacrylamide as disclosed in U.S. Pat. No. 6,391,937; pluronic 127, N-isopropylacrylamide (NiPAM); and blends (block copolymer, etc.) of all the above listed hydrogels.

Agarose is a linear polymer, made up of the repeating monomeric unit of agarobiose. Agarobiose is a disaccharide made up of D-galactose and 3,6-anhydro-L-galactopyranose. Agarose pectin or sulfonated agarose can be used as the hydrogel. Agarose can be obtained from Lonza (Rockland, Me.) under the brand name SeaKem™. In certain embodiments, the concentration of the agarose gel for effectively removing contaminants is from 0.1-2.0% w/v.

Purified agarose hydrogels may be purchased for use in the described method. An example of a commercial purified hydrogel can be obtained from Invitrogen (Carlsbad, Calif.) under the brand name E-Gel® EX Starter.

Polyacrylamide is a polymer ($-CH_2CHCONH_2-$) formed from acrylamide subunits. It can be synthesized as a simple linear-chain structure or cross-linked, typically using N,N'-methylenebisacrylamide. In the cross-linked form, polyacrylamide is highly water-absorbent, forming a soft gel. Polyacrylamide can be obtained from BioRad (Hercules, Calif.).

Purified polyacrylamide hydrogels may be purchased for use in the described method. An example of a commercial purified hydrogel can be obtained from BioRad (Hercules, Calif.).

Preconditioning of a medium can be performed. Preconditioning of a medium is often done to remove impurities found in the medium. For example, providing a potential across a hydrogel helps mobile impurities to migrate outside of the hydrogel. The potential can be, for example, 50V, 75V, 100V, 150V, 200V, 250V, 300V, 350V, 400V or 500V. In various embodiments, the potential can be provided for a period of time, such as at least 2 minutes, at least 5 minutes, at least 10 minutes, at least 15 minutes, at least 30 minutes, at least 45 minutes, at least 60 minutes, at least 120 minutes, or at least 180 minutes.

In various embodiments, the medium can be a filter. Examples of filters include those available from Pall Corporation (Port Washington, N.Y.), such as hydrophilic polypropylene, ahydrophilic, low binding material with pore sizes of 0.2 µm and 0.45 µm; polytetrafluoroethylene (PTFE), a hydrophobic, high binding material with pore sizes of 0.2 µm, 0.45 µm, 1 µm, 2 µm and 3 µm; glass fiber, a hydrophilic, moderate binding material with a pore size of 1 µm; nylon, a hydrophilic, low binding material with pore sizes of 0.2 µm and 0.45 µm; polyvinylidene fluoride (PVDF), a hydrophilic, low binding material with pore sizes of 0.2 µm and 0.45 µm; PES (Supor®), a hydrophilic, low binding material with pore sizes of 0.1 µm, 0.2 µm, 0.45 µm, and 0.8 µm; vinyl/acrylic copolymer, a hydrophobic material that may be used for air sampling and has pore sizes of 0.45 µm and 0.8 µm; polyvinyl chloride (PVC), which may also be used for air sampling and has pore sizes of 5 µm; hydrophilic mixed cellulose esters, a high binding material with a pore size of 0.45 µm; hydrophilic acrylic copolymer, which may be used as a pre-filter on a support and has pore sizes of 0.2 µm, 0.45 µm, 0.8 µm, 1.2 µm, 3 µm, and 5 µm; and nitrocellulose, a high binding material with a pore size of 0.2 µm. Examples of filters available from Millipore (Billerica, Mass.) include PTFE (LCR), a hydrophilic, moderate binding material with pore sizes of 0.2 µm and 0.45 µm; PVDF (Durapore™), a hydrophilic, low binding material with pore sizes of 0.2 µm and 0.45 µm; PTFE (Fluoropore™), a hydrophilic, low binding material with pore sizes of 0.2 µm and 0.45 µm; nylon, a hydrophilic, low binding material with pore sizes of 0.2 µm and 0.45 µm; glass fiber, a hydrophilic, moderate binding material with a pore size of 1 µm; and hydrophilic mixed cellulose esters, a high binding material with exemplary pore sizes of 0.2 µm, 0.45 µm, and 0.8 µm. Filters can have pore sizes of greater than or equal to about 0.01 µm, 0.05 µm, or 0.1 µm, 0.2 µm, 0.4 µm, 0.6 µm, 0.8 µm, 1.0 µm, 1.5 µm, 2.0 µm, 2.5 µm, 3.0 µm, 4.0 µm, or 5.0 µm. Filters can have pore sizes of less than or equal to about 5.0 µm, 4.0 µm, 3.0 µm, 2.5 µm, 2.0 µm, 1.5 µm, 1.0 µm, 0.8 µm, 0.6 µm, 0.4 µm, 0.2 µm, 0.05 µm, or 0.01 µm.

In various embodiments the method includes adding a chemical agent to the medium to increase the permeability of the medium and/or increase the ability of the contaminant to enter the medium.

Examples of chemical agents include reducing agents, including, but not limited to, dithiothreitol (DTT), tris(2-carboxyethyl)phosphine (TCEP), and mercaptoethanol reducing agents; denaturing agent using surfactants, including, but not limited to, sodium lauryl sulfates, non-ionic surfactants such as Triton X-100, Tween-20, or chaotropic agents, including, but not limited to, urea, thiourea, or guanidinium chloride; chelating agents that can coordinate molecules such as calcium, magnesium, and other divalent and trivalent ions (including metal ions), including ethylenediaminetetraacetic acid (EDTA) and ethylene glycol tetraacetic acid (EGTA); cleavage agents including proteases, nucleases, glyconases, lipases; and excipients such as polyethylene glycol. In some embodiments a combination of one or more chemical agents can be utilized.

Viscous gels include cellulose ethers (such as hydroxylethyl cellulose or Methocel™ (Dow (Midland, Mich.)) and soluble polymer viscosity modifiers (such as polyethylene glycol, polyvinylpyrrolidone, dextrans, pluronic surfactants, and alginates). In a viscous gel, the pore size is not defined. The separation is based on retarded flow of the cells in the viscous medium.

In some embodiments, agents can be added to or used to treat the medium to control electroosmotic flow. In some embodiments, it may be desirable to increase or decrease electroosmotic flow.

Sample Mixing

To analyze a representative sample, the sample should be substantially uniform. In some embodiments, the homogenization of a sample can be done by a sample mixing or stirring step. Mixing the sample acts to re-suspend any caked material formed on the walls of the well.

In various embodiments, the method includes mixing a sample using a pipette tip. See, for example, the pipette tip 228 in FIG. 2A. The sample is passed through the narrow opening of the pipette to shear and homogenize the sample.

Buffer Solutions

In various embodiments, the method includes placing a buffer in contact with the medium.

In some embodiments, the mixing parameters of the buffer are designed to maximize the removal of debris and non-target material.

In some embodiments, the buffer can be replenished to prevent accumulation of undesirable electrophoresis products. For example, undesirable effects pH gradients generated at the cathode and anode and in proximity to the sample can be substantially minimized by buffer replenishment or replacement, potentially using continuous flow.

In various embodiments, electrophoretic buffers utilize pairs of redox mediators. In certain embodiments, these redox mediators facilitate low voltage electrophoresis that permits cell viability to be maintained. These redox mediators may also enable the use of electrode materials that have limited utility in high voltage electrophoresis (for example, indium tin oxide, "ITO" electrodes). In addition, these redox mediators find use in "closed systems" (i.e., systems not open to the atmosphere). In closed systems, bubble formation and generation of other reactive species during the electrophoresis step, which can cause a number of problems, is prevented, and closed systems also help to prevent the exposure of the technician to potentially infectious samples, as well as reducing problems associated with discarding biological samples In some embodiments, the buffer is placed in a reservoir in contact with the medium. In various embodiments, the medium is not submerged in the buffer.

Buffers include, for example, various electrophoresis buffers including zwitterionic buffers, neutral buffers such as phosphate-buffered saline (PBS), lower or higher pH buffers, and hypotonic or hypertonic buffers. In some embodiments, borate and other selected ions and counter-ions are included to facilitate effective electrophoresis.

In some embodiments, the buffer solution includes histidine and tris(hydroxymethyl)aminomethane. Histidine has low conductivity. Tris(hydroxymethyl)aminomethane has some conductivity but has low mobility. Histidine has pKa values close to physiological values providing adequate buffering capacity. Tris(hydroxymethyl)aminomethane can be obtained from Sigma-Aldrich (St. Louis, Mo.) as Trizma® base (Sigma, T1503).

In some embodiments, the sample (in 150 mM NaCl) is desalted to remove cationic and anionic species that may interfere with subsequent analysis. In some embodiments, desalting allows successful concentration and capture of the microorganism.

Electrophoretic mobility can be buffer dependent due to zeta potential variability with salt concentration, valency of salts present in the buffer, and the pH of the buffer. Bacteria can lose charge as the concentration of salt increases or as the pH is lowered below a certain pH, for example, pH 5.0. Divalent and trivalent salts are more effective quenchers than monovalent salts. For example, $CaCl_2$ is more effective than NaCl to quench a charge. Certain agents such as chelators, including, but not limited to, ethylenediaminetetraacetic acid (EDTA) and ethylene glycol tetraacetic acid (EGTA), both available from Sigma-Aldrich, can be used to control the concentration of charged species in the sample.

Wells

Figure 8:
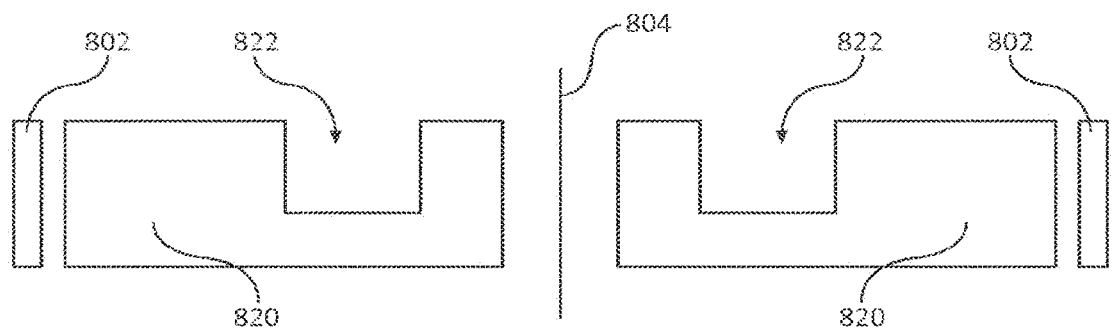
FIG. 8 is a side view of an embodiment of a circular well formed in a medium with corresponding electrodes

As shown in FIG. 2A, one or a plurality of wells can be formed in the medium. The wells are molded into the gel. For example, a custom well-forming comb can be used to create the appropriate well shape. Wells include side-walls that can be substantially vertical or diagonal. In various embodiments, the method includes wells that are non-rectangular shaped. In various embodiments, the wells are substantially chamfered to eliminate sharp edges in the well, enhancing target recovery. In some embodiments, the wells can hold various sample sizes. In various embodiments, the wells can hold from 10 µL to 500 µL. In some embodiments the wells are 5 to 250 mm wide. Multiple wells can be used for a sample. As illustrated in FIG. 8, a well 822 in medium 820 may be circular, surrounding an electrode such as cathode 804, and the counter electrodes may surround the well, such as the illustrated anode ring 802. In a circular well configuration, a sample placed in well 822 surrounds the cathode 804. In such an embodiment, a run buffer sheath may flow over cathode 804 to remove electrode byproducts during electrophoresis.

Figure 3:
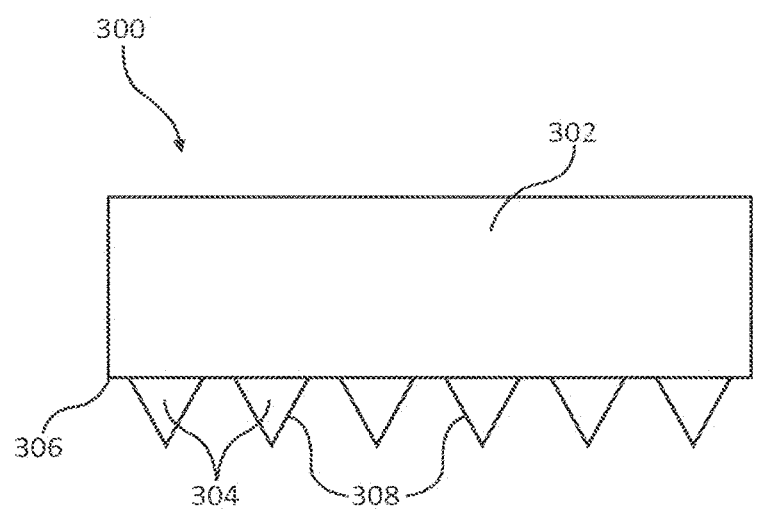
FIG. 3 is a side view of an embodiment of a custom well-forming comb used to make wells in a medium.

FIG. 3 depicts a side view of an embodiment of a custom well-forming comb 300. A comb body 302 has a plurality of well-forming teeth 304 connected to the comb body 302 by one edge 306. The sides of the teeth 308 form the side-walls of the non-rectangular shaped wells in a medium. In this embodiment the wells are triangular-shaped. The comb 300 is sized and shaped to fit the medium in a cassette, such as the cassette shown in FIG. 2A. In the illustrated embodiment, the comb 300 has six well-forming teeth 304, but could have more or less teeth depending on the size of the cassette.

In a rectangular or square bottomed well, sample solution can wick up the walls of the well. In a triangular shaped well, the sample solution does not tend as strongly to wick up the walls, making it easier to remove the microorganism from the well. In some embodiments, the triangular shaped well is narrowest at the bottom and widest at the top of the well. The well-forming teeth 304 shown in FIG. 3 create a pattern of triangular shaped wells in the medium. In other embodiments, the wells may be round-bottomed wells.

The samples can have high solids (e.g., from 1%-50% weight/volume of solid components). Minimizing the well width minimizes the caking of the solids on the well walls. In some embodiments, the well is 0.0025 inches wide at the widest point.

Chambers

Figure 9:
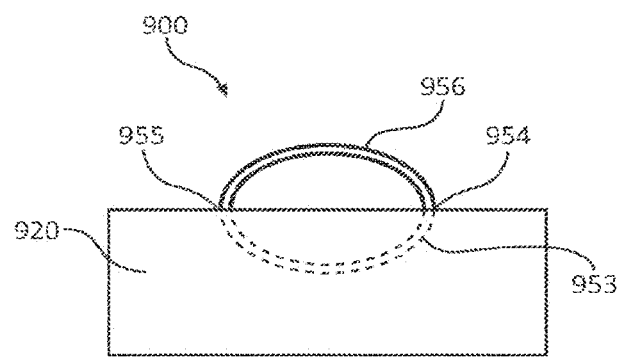
FIG. 9 is a side view of an embodiment of a chamber formed in the medium with an inlet and outlet port enabling sample recirculation.

In various embodiments, the method uses a system 900 wherein one or a plurality of chambers 953 can be formed in a medium 920. The chambers 953 are molded into the gel 920 and have an inlet and outlet port (954 and 955) as shown in FIG. 9. Inlet and outlet ports 954 and 955 are connected by tubing 956 for recirculating a sample through a chamber 953, such as by a peristaltic pump. The chambers may be submerged or partially submerged in buffer, and electrical potential is applied to the system orthogonally to the direction of the recirculating flow of sample.

Electrodes

In various embodiments of the method, an electrode or a plurality of electrodes may be contained within the well or chamber. Additionally, in various embodiments, the electrode or plurality of electrodes may be in contact with the medium or separated a distance from the medium. The electrode or plurality of electrodes may be connected to the medium using salt bridges, buffer, redox mediators, or other conductive charge transfer methods used by those skilled in the art or familiar with techniques used in applications for establishing faradaic current. In some embodiments the electrodes are in physical contact with the chamber walls.

In various embodiments, conductive materials may be utilized to distort the electric field resulting in localized concentration of cells and/or viruses. Electric field distortion may utilize material conductivity differences to accomplish the said localization.

Immobilization of the Cells and/or Viruses

In various embodiments, the method includes immobilizing the microorganism. Cells and/or viruses are immobilized by various filters that exclude the targets (microorganism) from penetrating, for example, tube walls, microchannels (horizontal or vertical), or any geometry that uses a capture surface (specific or nonspecific), mazes, fluidic dead space (eddy cul-de-sacs), and microwells of approximate cellular scale.

Detection Surface

In some embodiments, the method includes immobilization of cells and/or viruses on a positively charged surface. For example, cells and/or viruses can be immobilized by a positively charged detection surface. In other embodiments, the cells and/or viruses may be immobilized by embedding in the medium.

Detection surfaces are disclosed in, for example, U.S. Pat. No. 6,844,028, incorporated by reference herein in its entirety. Detection surfaces can include those coated with poly-L-lysine, polyethylenimine, or other cationic polymers. Additionally, detection surfaces can include hydrophobic surface coatings.

After the contaminants are removed from the sample by the medium, the microorganism can be detected by a system. In some embodiments, the system is an optical sensing system. In some embodiments, the system is a microscope.

In some embodiments, the system is an automated system.

In various embodiments, the sequential or simultaneous use of a plurality of electrophoresis electrodes allows multidimensional electrophoresis, i.e., the solution may be targeted, "mixed," or "stirred" in the vicinity of a detection surface to further increase the kinetics of binding. For example, polarities can be reversed to allow cells and/or viruses that may not have bound to the detection surface to travel back "over" the surface, resulting in increased binding. Also, electrodes may be located and field polarity switched according to a programmed sequence so as to provide agitation in two dimensions of a plane, or in three dimensions.

Detection of the Microorganism

In various embodiments, the method includes detection of the microorganism. In general, biosensor devices are designed to fit into a detection unit, and generally utilize a number of components, which can either be "on-chip" (e.g., part of a biosensor cartridge) or "off-chip" (where some of the components are part of separate device or devices into which the biosensor cartridge fits). These components include, but are not limited to, one or a plurality (e.g., an array) of detection surface(s), concentration modules (which, as outlined herein, frequently are configured with the detection surface(s)), detection modules (again, frequently configured with the detection surface(s)), input and output ports, channels, pumps, mixers, valves, heaters, fluid reservoirs (including sample reservoirs, reagent reservoirs, and buffer reservoirs), concentration controllers (e.g., in the case of electrophoresis, electrical controllers), and data collection and analysis (e.g., computer) components.

An example of a microorganism diagnostic system is described in U.S. patent application Ser. No. 10/888,828 filed Jul. 8, 2004, issued as U.S. Pat. No. 7,687,239, and U.S. application Ser. No. 11/303,803, filed Dec. 16, 2005, issued as U.S. Pat. No. 7,341,841, both of which are incorporated herein by reference in their entirety.

Low levels of cells and/or viruses can be detected with this method. Cells can be measure in terms of cells per mL, colony forming units (CFU, or units) per mL for fungi and/or bacterial microorganisms, and viruses can be measured in particles per mL or plaque forming units per mL (PFU). Levels of cells and/or viruses are described in units per volume, typically per mL volume. Those skilled in the art understand the specific units are typically reported as appropriate for a given target. For exemplary purposes, the concentration ranges below are reported in generic units per mL. For example, levels of 0.1 to $1\times10^8$ units/mL can be detected. In various embodiments, cells and/or viruses of levels less than $5\times10^8$ units/mL, $3\times10^8$ units/mL, $1\times10^8$ units/mL, $0.8\times10^8$ units/mL, $0.6\times10^8$ units/mL, $0.4\times10^8$ units/mL, $0.2\times10^8$ units/mL, or $0.1\times10^8$ units/mL, can be detected.

EXAMPLES

The following examples are provided for illustration purposes and are not intended to limit scope. Other variants will be readily apparent to one of ordinary skill in the art and are encompassed by the appended claims.

The example described below anticipates a wide range of specimen variability, first homogenizing the specimen, then sampling the specimen, and then purifying the sample to remove debris and other interfering materials by placing the sample in a medium containing a well and applying a potential laterally across the medium to retain cells and pass contaminants into the medium.

Example 1

Purification of Bacteria Cells from Respiratory Specimens

Gel Preparation 10 grams of agarose powder (SeaKem, LE Agarose) was mixed with 1 L of buffered solution containing 100 mM histidine (Sigma, H8000) and 2.5 mM Trizma® base (Sigma, T1503). The final concentration of agarose slurry was 1.0% (w/v). The solution was boiled to melt the agarose powder and the molten agarose was stored in liquid form at 40° C. until use.

Gel Casting

Those familiar in the art of gel slab electrophoresis recognize that solid inserts or combs are routinely used to create a void volume in a gel slab that is later utilized for sample loading. Gel electrophoresis combs are generally nominally 1-2 mm thick, capable of holding nominally 100 µL of sample volume. In this example, a custom equilateral V-shaped well was used. The well had sides 1 cm long and a thickness of nominally 0.6 mm (0.025"). The comb was inserted into a gel box container (E-C Apparatus, EC 250-90) and the box filled with the molten agarose submerging a portion of the comb. The agarose was allowed to cool to room temperature forming an agarose gel. The comb was removed from the solidified agarose and the void volume of the comb formed a well in the material. The V-shaped well enabled facile recovery of the sample volume from the well, described in further detail below.

Pretreatment of the Agarose Gel Medium

The gel box containing the agarose gel medium having triangular wells was placed in an electrophoresis apparatus and then submerged in a run buffer containing 100 mM histidine and 2.5 mM Trizma® base. A 250 volt potential was applied for 1 hr. The applied potential yielded 22 mA of current. The pretreated gels were removed from the electrophoresis apparatus and transferred to a closed container and stored submerged in fresh run buffer until use.

Specimen Homogenization

A remnant specimen having a known level of bacteria was homogenized by pouring into a syringe connected to 0.02" (0.5 mm) inner diameter PEEK tubing and forcing through the PEEK tubing 10 times at a flow rate of approximately 0.1 mL/sec to liquefy the specimens. The specimen was then filtered through 5 µm track etch polycarbonate filters (SPI Pore, E5013-MB). A 1 mL sample aliquot of the specimen was processed as described below. An aliquot of the specimen was also reserved as a control.

A control or a known clinical sample (e.g., with a known concentration of bacteria) can be compared to the unknown sample.

Assessment of the Sample

The sample was diluted to a final nominal bacterial concentration of $1.5\times10^3$ CFU/mL. 50 µL of the diluted sample was plated in triplicate on Mueller Hinton Agar (MHA) and placed in the incubator overnight. The number of colonies counted on the overnight incubated plates divided by the plated volume and multiplied by dilution factor yielded the actual number of input *Klebsiella oxytoca* bacteria in CFU/mL.

The sample was diluted 10-fold and the optical density read was acquired at 625 nm to assess the amount of particulate debris in the sample.

Sample Loading

The pretreated gels were placed in the gel box and apparatus, patted dry, and excess liquid was removed from the triangular wells using 0.2 mm thick flat capillary plastic pipette tips (Fisher 07-200-519). The well was filled with a 20 μL sample of the homogenized specimen.

Sample Treatment

Histidine/Tris run buffer was added to the apparatus so that the liquid level was below the top of the gel slab. The sample was electrophoresed for 5 minutes at 250 volts and the samples were hydrodynamically sheared by pipetting the sample volume up and down 5x using a capillary pipette tip. The samples were electrophoresed again for 5 minutes at 250 volts and the samples then hydrodynamically sheared by pipetting the sample volume up and down 5x using a capillary pipette tip.

Post-Treatment Assessment of Spiked Sample

The treated sample was diluted to a final concentration of $1.5 \times 10^3$ CFU/mL. 50 μL of the diluted sample was plated in triplicate on Mueller Hinton Agar (MHA) and place in the incubator overnight. The number of colonies counted on the overnight incubated plates divided by the plated volume and multiplied by dilution factor yielded the actual number of *Klebsiella oxytoca* bacteria recovered in CFU/mL.

The treated sample was diluted 10-fold and then the optical density read was acquired at 625 nm to assess the amount of particulate debris remaining in the sample.

Results

|  | Pre-Treatment Optical Density (OD) | Post-Treatment Optical Density (OD) | Fold Cleanup |
| --- | --- | --- | --- |
| MEDIA METHOD | 0.2841 | 0.065 | 4.35 |

Electrode Configuration and Circuit Details

The 20 μL of recovered sample volume was diluted with 40 μL of 10 mM ascorbic acid and then introduced into a flow cell (described below) for electrokinetic concentration.

For comparison purposes, a 20 μL of a non-treated sample was diluted with 40 μL of 10 mM ascorbic acid and then introduced into a flow cell (described below) for electrokinetic concentration.

Flow Cell Construction

Figure 4A:
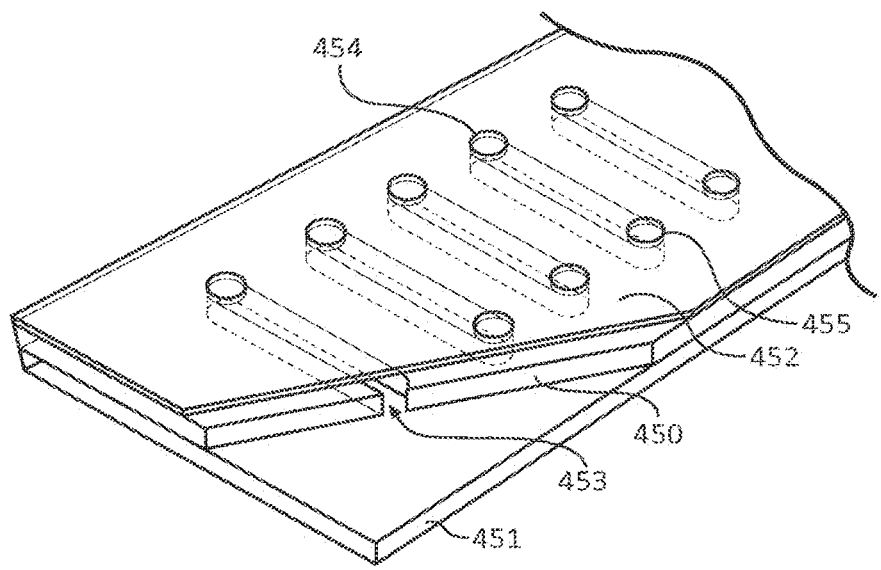
FIGS. 4A and 4B are a perspective view of multiple flow cell laminate assembly and a single flow cell cutaway view with corresponding electrode and circuit details used to create a potential across a medium.
Figure 4B:
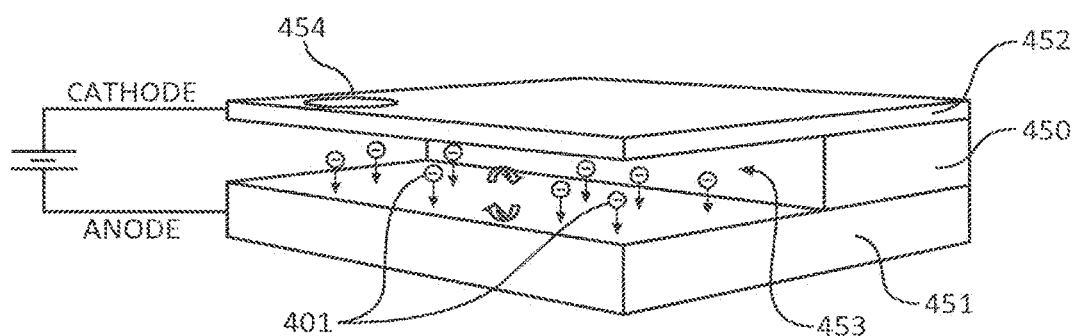

FIG. 4A is a perspective view of a multiple flow cell laminate flow cell assembly 400, and FIG. 4B is a single flow cell cutaway view with corresponding electrode and circuit details. Flow cells were assembled using a three layer die-cut laminate flow cell assembly 450 (DLE, Oceanside, Calif.), sandwiched between an indium tin oxide (ITO) coated glass slide flow cell floor 451 (Delta Technology, Stillwater, Minn.) and an ITO coated 5 mil polyester (ITO PET) plastic flow cell ceiling 452 (Sheldahl, Northfield, Minn.) forming a fluidic flow cell chamber. The laminate flow cell assembly contained 32 separate channels 453, each having 1.78 mm width×0.30 mm height×11.28 mm length, with 1.78 mm diameter fluidic inlet and outlet ports (454 and 455, respectively) to interface with plastic pipette tips for fluid exchanges using manual pipettors. The transparent top and bottom electrodes enabled microscope imaging.

Bacteria 401 suspended in redox active EKB were contacted with uniform transparent electrodes constructed from transparent ITO coated glass (Delta Technologies, Stillwater, Minn.) or polyester film (Sheldahl, Northfield, Minn.). A potential was applied to the conductive ITO surfaces completing the circuit, establishing a faradaic current and an electric field between the electrodes and enabling bacterial electrokinetic concentration (EKC) and surface immobilization, as illustrated in FIG. 4B.

Bacterial Suspension and Surface Concentration Experiments

Studies were performed by loading the flow cells with samples, with the power supply turned off, and then inserting the flow cells onto the microscope stage. The microscope acquired images at the bottom flow cell surface during subsequent steps. The power supply was connected and cells electrokinetically concentrated to the flow cell's bottom surface by application of a 1.4V DC fixed potential. The top electrode (flow cell ceiling) was connected to the negative power supply terminal, and the bottom electrode (flow cell floor) was connected to the positive terminal. The applied potential resulted in complete bacterial concentration in less than 3 minutes. After 300 seconds, a −1.0 V DC fixed potential was applied for an additional 60 seconds to measure the degree of irreversible binding of the sample debris and bacteria on the flow cell floor. The digital microscope acquired images every 3-7 seconds during concentration.

Digital Microscopy Setup

An Olympus IX-71 inverted microscope equipped with a 12-bit, 1200×1600 pixel array monochrome CCD digital camera (MicroFire, Leeds Precision Instruments, Minneapolis, Minn.) was used for image acquisition. The transmitted illumination cone, created with an IX-PH3 annular ring placed in a 0.55 NA transmitted light condenser, was 33.4° from the normal to the microscope's focal plane. The illumination cone, after refraction through the flow cell's air-glass-ITO-liquid interfaces (described below), resulted in a 24.5° forward scatter angle-of-incidence relative to the focal plane normal. The forward scatter angle-of-incidence relative to the flow cell's air-plastic-ITO-liquid interfaces was not calculated. In all formats, a dark image was obtained in the absence of scatterers, as the illumination cone passed outside the 20×, 0.4 NA microscope objective's (LCPlanFl Olympus, Leeds Precision Instruments) imaging cone. The presence of scatterers resulted in the appearance of bright objects on a dark image background (dark-field image for objects within the focal depth). The system field-of-view was 444×592 μm with corresponding 0.37 μm pixel resolution. The imaging system's depth-of-focus and image depth were 5.8 μm and 3.8 mm respectively. Constant camera exposure and gain settings were maintained when relative intensity comparisons were performed, as in the case of growth experiments described below.

Accumulation Time Results

Figure 5:
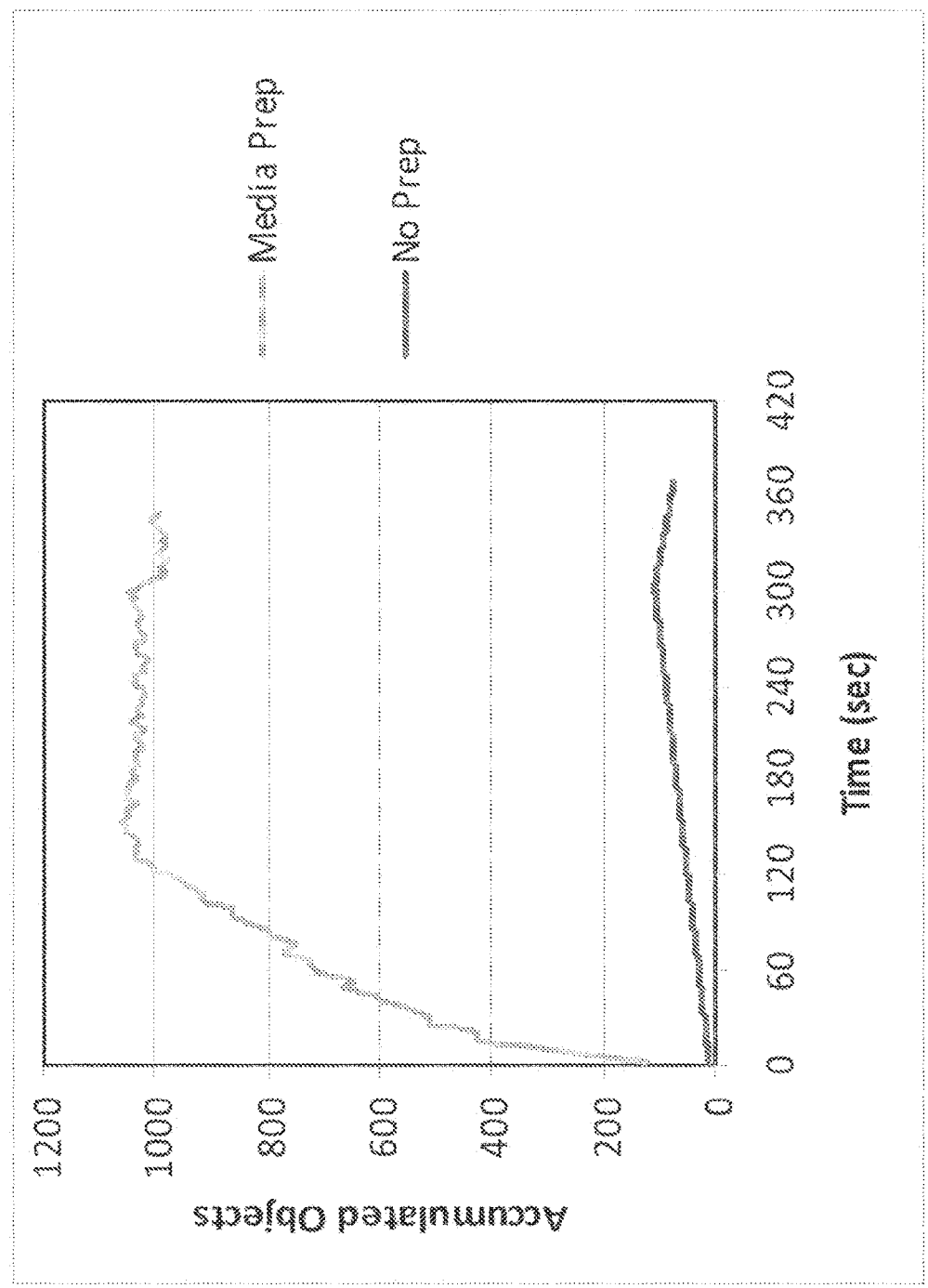
FIG. 5 is a graph showing results of accumulated objects (solid materials immobilized on a surface) over time for treated compared to non-treated samples.

FIG. 5 is a graph showing results of accumulated objects over time for treated compared to non-treated samples. The non-treated sample data is expected data.

The objects are solid material, such as cells, viruses, and cellular debris, that are immobilized on a sample surface. FIG. 5 shows that material concentrates, and then adheres to, the surface. Subsequent processes, such as measuring the growth or growth rate, can be utilized to determine the number of viable cells, and additionally probing the material using receptor-ligand binding techniques, including, but not limited to, antibody recognition or nucleic acid hybridization methods can be used to measure the abundance of microorganisms present.

Figure 6A:
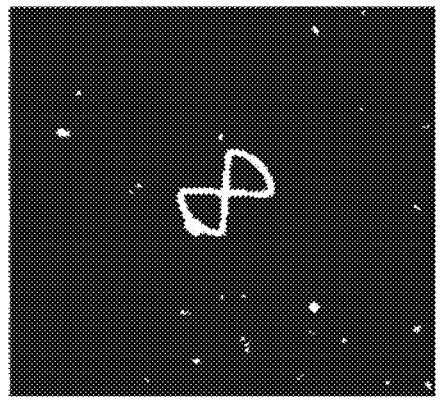
FIGS. 6A, 6B and 6C depict microscopic images of non-treated samples over time.
Figure 6B:
Figure 6C:
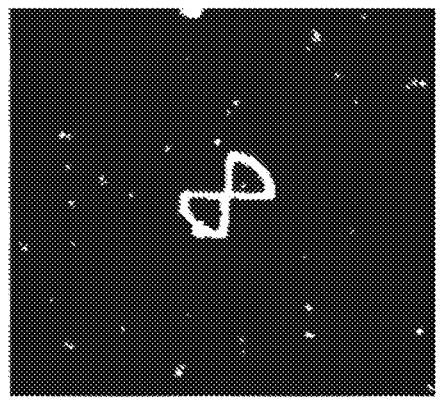

FIGS. 6A, 6B and 6C depict microscopic images of non-treated samples at initial time, time of 300 seconds, and time of 360 seconds, respectively. The surface accumulation rate is low. As shown in FIGS. 6A, 6B and 6C, poor surface retention of the objects occurs when samples are not treated.

Figure 7A:
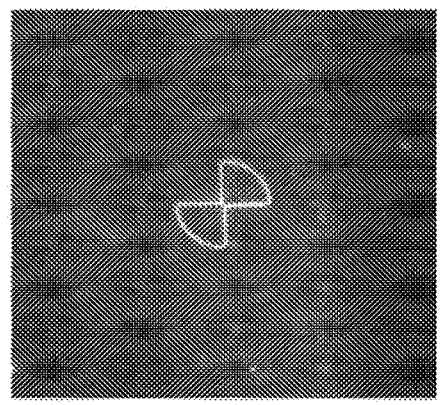
FIGS. 7A, 7B and 7C depict microscopic images of treated samples over time.
Figure 7B:
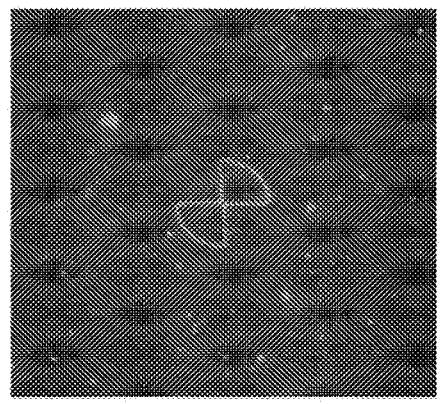
Figure 7C:
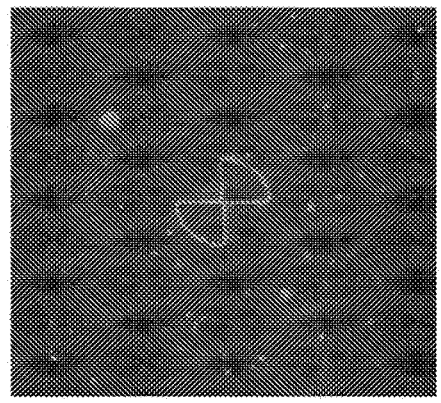

FIGS. 7A, 7B and 7C depict microscopic images of treated samples at initial time, time of 300 seconds, and time of 360 seconds, respectively. The treated sample surface accumulates all objects, as evidenced by a plateau occurring in less than 3 minutes. As shown in FIGS. 7A, 7B and 7C, the objects were irreversibly bound to the surface, as evidenced by consistent accumulated counts during reverse electrophoresis.

Bacterial Growth

After cell immobilization, the flow cell was rinsed with 10 times the internal cell volume of ⅒th strength cation-adjusted Mueller-Hinton Broth (CAMHB) growth media (Difco, Sparks, Md.). 100 µL of liquefied Mueller Hinton Agar (MHA) was loaded into the flow cell and then cooled to room temperature, solidifying into a hydrogel.

Time Lapse Imaging

Direct observation of bacterial growth was performed by inserting the disposable 32-channel flow cell assembly into a custom benchtop automated instrument that combined digital microscopy, motion control, and image analysis software. The system was enclosed in an incubator maintained at 35° C. The motorized microscope stage enabled automated XY translation, location logging, and memory with 10 µm repeatability. The system automatically focused and acquired surface images of adherent bacteria at programmed time intervals for multiple fields-of-view during an experiment. The system used the fiducial markings to autofocus and mechanically align (±1 pixel) the fields-of-view prior to image acquisition. Unless stated otherwise, a single field-of-view contained sufficient numbers of cells for analysis, and automated analysis routines counted the number of growing clones.

Growth Results

The number of growing clones observed using the digital microscope method was compared with the number of expected growing clones, assuming 100% yield and a 1 to 1 correlation between growing colonies on MHA plates, to calculate a digital microscopy method efficiency. The medium method was compared to an alternative medium method wherein the gel was submerged. A total efficiency was calculated by multiplying the treatment recovery and digital microscopy efficiency.

|  | Post Treatment Recovery | Digital Microscopy EFF | Total EFF |
| --- | --- | --- | --- |
| Control - No Prep | 100% | 12% | 12% |
| Medium Method | 82% | 90% | 74% |
| Submerged Medium Method | 43% | 100% | 43% |

The total efficiency for the medium method was highest when the gel slab was not submerged.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily imply that two elements are directly connected and in fixed relation to each other. The exemplary drawings are for purposes of illustration only, and the dimensions, positions, order and relative sizes reflected in the drawings attached hereto may vary.

Numerous and varied other arrangements can be readily devised by those skilled in the art without departing from the spirit and scope of the description. Moreover, all statements herein reciting principles, aspects and embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure. All references cited herein are incorporated by reference in their entirety.

The invention claimed is:

1. A method of quantifying growth of one or more purified microorganisms, comprising:
adding a sample containing contaminants and one or more microorganisms to a well disposed in a porous medium;
applying an electrical potential across the medium to cause the contaminants to enter the porous medium through one or more walls of the well while retaining the one or more microorganisms in the well;
reversing the electrical potential for a sufficient time to displace the one or more microorganisms from a surface of the one or more walls of the well in the porous medium, thereby purifying the one or more microorganisms;
introducing the one or more purified microorganisms to a flow cell;
embedding the one or more purified microorganisms in an embedding medium, thereby immobilizing the one or more microorganisms in the flow cell;
imaging the one or more purified microorganisms using automated digital microscopy; and
quantifying growth of the one or more purified microorganisms over a period of time using imaging data.

2. The method of claim 1, wherein applying the electrical potential and reversing the electrical potential are performed iteratively.

3. The method of claim 1, wherein the one or more purified microorganisms are bacteria.

4. The method of claim 1, wherein the embedding medium comprises agar.

5. The method of claim 3, wherein the embedding medium comprises agar.

6. The method of claim 4, wherein the sample is mixed at least one of before applying the electrical potential, during application of the electrical potential, and after applying the electrical potential.

7. The method of claim 1, wherein the sample contains between 0.1 and $1 \times 10^8$ units/mL of microorganisms.

8. The method of claim 3, wherein the sample contains between 0.1 and $1 \times 10^8$ units/mL of microorganisms.

9. The method of claim 1, wherein the sample comprises a blood sample.

10. The method of claim 1, wherein the sample comprises a lung sample.

11. The method of claim 1, wherein the sample comprises a urine sample.

12. The method of claim 1, wherein the porous medium comprises a hydrogel.

* * * * *